United States Patent
Paz

(10) Patent No.: US 11,264,125 B2
(45) Date of Patent: Mar. 1, 2022

(54) IMAGE RECOGNITION-BASED DOSAGE FORM DISPENSERS

(71) Applicant: DOSENTRX LTD, Bet Shemesh (IL)

(72) Inventor: Ilan Paz, Alon Shvut (IL)

(73) Assignee: Dosentrx, Ltd., Bet Shemesh (IL)

( * ) Notice: Subject to any disclaimer, the term of this patent is extended or adjusted under 35 U.S.C. 154(b) by 662 days.

(21) Appl. No.: 15/768,459

(22) PCT Filed: Oct. 13, 2016

(86) PCT No.: PCT/IL2016/051109
§ 371 (c)(1),
(2) Date: Apr. 13, 2018

(87) PCT Pub. No.: WO2017/064709
PCT Pub. Date: Apr. 20, 2017

(65) Prior Publication Data
US 2018/0296442 A1    Oct. 18, 2018

Related U.S. Application Data

(60) Provisional application No. 62/406,012, filed on Oct. 10, 2016, provisional application No. 62/241,808, filed on Oct. 15, 2015.

(51) Int. Cl.
*G16H 30/20* (2018.01)
*A61J 7/00* (2006.01)
(Continued)

(52) U.S. Cl.
CPC .............. *G16H 30/20* (2018.01); *A61J 1/035* (2013.01); *A61J 7/0053* (2013.01); *A61J 7/0418* (2015.05);
(Continued)

(58) Field of Classification Search
CPC .... A61M 2210/0618; A61M 2210/005; A61M 15/0021; A61M 15/0065; A61M 15/009;
(Continued)

(56) References Cited

U.S. PATENT DOCUMENTS

| 38,343 A | 4/1863 | Tower |
| 708,216 A | 9/1902 | Fowler, Jr. |

(Continued)

FOREIGN PATENT DOCUMENTS

| CN | 101495080 | 7/2009 |
| DE | 2240410 A1 | 2/1974 |

(Continued)

OTHER PUBLICATIONS

PCT/IL2016/051109, International Search Report and Written Opinion, dated Mar. 14, 2017, 9 pages.
(Continued)

*Primary Examiner* — Brandy S Lee
(74) *Attorney, Agent, or Firm* — Armstrong Teasdale LLP

(57) ABSTRACT

This invention provides a dosage form dispenser, comprising a casing comprising a first portion adapted for insertion within an oral cavity of a subject and a second portion adapted to encase a dosage form dispensing mechanism located therewithin; at least one camera positioned on said second portion of said casing, further positioned to capture a field of view of a portion of a face of a subject, wherein said field of view comprises at least a portion of a base view of the nose of said subject; a dosage form dispensing mechanism; a microprocessor and associated memory for processing and storing user authentication information, comparing images relayed from said at least one camera to at least one stored user standard and providing authentication when a match is established; and an interface connected to said dispensing mechanism, which promotes dispensing (Continued)

said dosage form when said authentication has been obtained. Methods for dispensing a dosage form directly within an oral cavity of a subject in need thereof, using the dispensers are also described.

31 Claims, 10 Drawing Sheets

(51) Int. Cl.
    *A61M 15/00*     (2006.01)
    *A61M 16/04*     (2006.01)
    *G16H 40/63*     (2018.01)
    *G16H 50/20*     (2018.01)
    *A61J 7/04*     (2006.01)
    *G16H 20/13*     (2018.01)
    *A61J 1/03*     (2006.01)
    *G06K 9/00*     (2022.01)
    *A61B 5/1171*     (2016.01)
    *A61B 5/00*     (2006.01)

(52) U.S. Cl.
    CPC .......... *A61J 7/0481* (2013.01); *A61M 15/009* (2013.01); *A61M 15/0021* (2014.02); *A61M 15/0065* (2013.01); *A61M 16/0493* (2014.02); *G06K 9/00255* (2013.01); *G06K 9/00281* (2013.01); *G06K 9/00288* (2013.01); *G16H 20/13* (2018.01); *G16H 40/63* (2018.01); *G16H 50/20* (2018.01); *A61B 5/1176* (2013.01); *A61B 5/4277* (2013.01); *A61J 2200/30* (2013.01); *A61J 2205/40* (2013.01); *A61J 2205/70* (2013.01); *A61M 2205/13* (2013.01); *A61M 2205/3303* (2013.01); *A61M 2205/3306* (2013.01); *A61M 2205/3313* (2013.01); *A61M 2205/502* (2013.01); *A61M 2205/52* (2013.01); *A61M 2205/581* (2013.01); *A61M 2205/583* (2013.01); *A61M 2205/8206* (2013.01); *A61M 2210/0618* (2013.01); *A61M 2230/432* (2013.01); *A61M 2230/50* (2013.01)

(58) Field of Classification Search
    CPC .......... A61M 16/0493; A61M 2205/13; A61M 2205/3303; A61M 2205/3306; A61M 2205/3313; A61M 2205/502; A61M 2205/52; A61M 2205/581; A61M 2205/583; A61M 2205/8206; A61M 2230/432; A61M 2230/50; A61B 5/1176; A61B 5/4277; A61J 7/0481; A61J 1/035; A61J 2200/30; A61J 2205/40; A61J 2205/70; A61J 7/0053; A61J 7/0418; G16H 20/13; G16H 30/20; G16H 40/63; G16H 50/20

See application file for complete search history.

(56) References Cited

U.S. PATENT DOCUMENTS

| | | |
|---|---|---|
| 1,187,634 A | 6/1916 | Lorimer et al. |
| 2,004,243 A | 6/1935 | Hloch |
| 2,470,298 A | 5/1949 | Fields |
| 2,510,712 A | 6/1950 | Olowinski |
| 2,526,749 A | 10/1950 | Hokanson |
| 2,694,641 A | 11/1954 | Atwood |
| 2,740,558 A | 4/1956 | Steele |
| 2,963,200 A | 12/1960 | Miller |
| 3,150,639 A | 9/1964 | Sereda |
| 3,270,918 A | 9/1966 | Burch et al. |
| RE26,589 E | 5/1969 | Murov et al. |
| 3,923,060 A | 12/1975 | Ellinwood, Jr. |
| 4,106,698 A | 8/1978 | Lin |
| 4,114,965 A | 9/1978 | Oye et al. |
| 4,695,954 A | 9/1987 | Rose et al. |
| 4,839,806 A | 6/1989 | Goldfischer et al. |
| 4,887,594 A | 12/1989 | Siegel |
| 4,918,690 A | 4/1990 | Markkula, Jr. |
| 5,049,125 A | 9/1991 | Accaries et al. |
| 5,110,008 A | 5/1992 | Moulding et al. |
| 5,163,426 A | 11/1992 | Czeisler et al. |
| 5,176,133 A | 1/1993 | Czeisler et al. |
| 5,219,093 A | 6/1993 | Moulding et al. |
| 5,344,043 A | 9/1994 | Moulding et al. |
| 5,431,299 A | 7/1995 | Brewer et al. |
| 5,460,299 A | 10/1995 | Prause |
| 5,475,687 A | 12/1995 | Markkula, Jr. et al. |
| 5,490,610 A | 2/1996 | Pearson |
| 5,524,073 A | 6/1996 | Stambler |
| 5,562,232 A | 10/1996 | Pearson |
| 5,844,888 A | 12/1998 | Markkula, Jr. |
| 5,850,937 A | 12/1998 | Rauche |
| 5,853,244 A | 12/1998 | Hoff et al. |
| 5,955,952 A | 9/1999 | Bergman et al. |
| 6,032,155 A | 2/2000 | de la Huerga |
| 6,048,271 A | 4/2000 | Barcelou |
| 6,068,126 A | 5/2000 | Dejonge |
| 6,150,942 A | 11/2000 | O'Brien et al. |
| 6,152,364 A | 11/2000 | Schoonen et al. |
| 6,163,736 A | 12/2000 | Halfare |
| 6,219,587 B1 | 4/2001 | Ahlin et al. |
| 6,263,259 B1 | 7/2001 | Bartur |
| 6,318,051 B1 | 11/2001 | Preiss |
| 6,327,570 B1 | 12/2001 | Stevens |
| 6,352,200 B1 | 3/2002 | Schoonen et al. |
| 6,579,231 B1 | 6/2003 | Phipps |
| 6,601,729 B1 | 8/2003 | Papp |
| 6,604,019 B2 | 8/2003 | Ahlin et al. |
| 6,611,733 B1 | 8/2003 | De La Huerga |
| 6,729,327 B2 | 5/2004 | McFarland, Jr. et al. |
| 6,776,304 B2 | 8/2004 | Liff et al. |
| 6,814,255 B2 | 11/2004 | Liff et al. |
| 6,848,593 B2 | 2/2005 | Papp |
| 6,892,941 B2 | 5/2005 | Rosenblum |
| 6,922,664 B1 | 7/2005 | Fernandez et al. |
| 6,947,900 B2 | 9/2005 | Giordano, III et al. |
| 6,988,634 B2 | 1/2006 | Varis |
| 7,006,894 B2 | 2/2006 | de la Huerga |
| 7,084,946 B2 | 8/2006 | Ota et al. |
| 7,178,688 B2 | 2/2007 | Naufel et al. |
| 7,216,776 B2 | 5/2007 | Gelardi |
| 7,216,802 B1 | 5/2007 | De La Huerga |
| 7,231,920 B2 | 6/2007 | Harvey et al. |
| 7,302,311 B2 | 11/2007 | Varis |
| 7,426,475 B1 | 9/2008 | Tangellapally et al. |
| 7,451,761 B2 | 11/2008 | Hickey et al. |
| 7,491,219 B2 | 2/2009 | Steinberg |
| 7,503,081 B2 | 3/2009 | Montgomery |
| 7,624,733 B2 | 12/2009 | Riley et al. |
| 7,624,894 B2 | 12/2009 | Gerold et al. |
| 7,637,079 B2 | 12/2009 | Klingel et al. |
| 7,654,261 B1 | 2/2010 | Rockhold |
| 7,665,811 B2 | 2/2010 | Johanning |
| 7,677,941 B2 | 3/2010 | Koyama |
| 7,692,195 B2 | 4/2010 | Namose |
| 7,704,236 B2 | 4/2010 | Denolly |
| 7,727,469 B2 | 6/2010 | Takahashi et al. |
| 7,766,365 B2 | 8/2010 | Darling, III |
| 7,771,984 B2 | 8/2010 | Dzekunov et al. |
| 7,787,986 B2 | 8/2010 | Pinney et al. |
| 7,844,362 B2 | 11/2010 | Handfield et al. |
| 7,860,724 B2 | 12/2010 | Chudy et al. |
| 7,865,263 B2 | 1/2011 | Spano, Jr. et al. |
| 7,885,725 B2 | 2/2011 | Dunn |
| 7,930,056 B2 | 4/2011 | Fernandez |
| 7,932,832 B2 | 4/2011 | Hayashi |
| 7,934,355 B2 | 5/2011 | Strub et al. |
| 7,946,483 B2 | 5/2011 | Miller et al. |
| 7,978,083 B2 | 7/2011 | Melker et al. |
| 7,988,016 B2 | 8/2011 | Klein et al. |
| 7,996,106 B2 | 8/2011 | Ervin |

(56) References Cited

U.S. PATENT DOCUMENTS

| | | |
|---|---|---|
| 7,999,987 B2 | 8/2011 | Namose |
| 8,006,903 B2 | 8/2011 | Braun |
| 8,015,417 B2 | 9/2011 | Kato et al. |
| 8,027,748 B2 | 9/2011 | Handfield et al. |
| 8,032,397 B2 | 10/2011 | Lawless |
| 8,065,035 B2 | 11/2011 | Ross et al. |
| 8,073,563 B2 | 12/2011 | Vahlberg et al. |
| 8,090,473 B2 | 1/2012 | Higham |
| 8,103,346 B2 | 1/2012 | Mass et al. |
| 8,103,379 B2 | 1/2012 | Biba et al. |
| 8,112,942 B2 | 2/2012 | Bohm et al. |
| 8,118,222 B2 | 2/2012 | Barcelou |
| 8,126,590 B2 | 2/2012 | Vahlberg et al. |
| 8,135,497 B2 | 3/2012 | Joslyn |
| 8,140,186 B2 | 3/2012 | Vahlberg et al. |
| 8,145,353 B1 | 3/2012 | Cotner |
| 8,162,690 B2 | 4/2012 | Smith |
| 8,195,329 B2 | 6/2012 | Pinney et al. |
| 8,265,757 B2 | 9/2012 | Mass et al. |
| 8,266,447 B2 | 9/2012 | Völkening et al. |
| 8,280,550 B2 | 10/2012 | Levy et al. |
| 8,343,434 B2 | 1/2013 | Hyde et al. |
| 8,390,761 B2 | 3/2013 | Oda |
| 8,395,314 B2 | 3/2013 | Yamamoto et al. |
| 8,417,378 B2 | 4/2013 | Joslyn |
| 8,468,031 B2 | 6/2013 | Jung et al. |
| 8,478,604 B2 | 7/2013 | Henderson et al. |
| 8,494,878 B2 | 7/2013 | Stevens |
| 8,504,197 B2 | 8/2013 | Farr |
| 8,554,365 B2 | 10/2013 | Thomas et al. |
| 8,587,427 B2 | 11/2013 | Lalonde et al. |
| 8,615,971 B2 | 12/2013 | Freudelsperger |
| 8,626,342 B2 | 1/2014 | Williams |
| 8,672,879 B2 | 3/2014 | Grant et al. |
| 8,725,291 B2 | 5/2014 | Czaja et al. |
| 8,787,555 B2 | 7/2014 | Gonen et al. |
| 8,926,526 B2 | 1/2015 | Shuck |
| 8,930,207 B2 | 1/2015 | Keravich et al. |
| 8,954,190 B2 | 2/2015 | Braunstein |
| 9,014,847 B2 | 4/2015 | Dunn |
| 9,031,690 B2 | 5/2015 | Cotner |
| 9,037,616 B2 | 5/2015 | Bessette |
| 9,043,012 B2 | 5/2015 | Davey et al. |
| 9,066,847 B2 | 6/2015 | Poutiatine et al. |
| 9,098,983 B2 | 8/2015 | Rahilly |
| 9,107,571 B2 | 8/2015 | Strauss et al. |
| 9,111,408 B2 | 8/2015 | Biba et al. |
| 9,185,501 B2 | 11/2015 | Pai |
| 9,211,498 B2 | 12/2015 | Akdogan et al. |
| 9,235,689 B2 | 1/2016 | Ervin |
| 9,242,043 B2 | 1/2016 | Ludolph |
| 9,245,305 B2 | 1/2016 | Wellington et al. |
| 9,358,499 B2 | 6/2016 | Akdogan et al. |
| 9,358,500 B2 | 6/2016 | Akdogan et al. |
| 9,361,748 B2 | 6/2016 | Cunningham et al. |
| 9,381,311 B2 | 7/2016 | Holakovsky et al. |
| 9,400,873 B2 | 7/2016 | Kamen et al. |
| 9,443,062 B2 | 9/2016 | Long et al. |
| 9,463,412 B2 | 10/2016 | Akdogan et al. |
| 9,465,919 B2 | 10/2016 | Kamen et al. |
| 9,508,935 B2 | 11/2016 | Watanabe |
| 9,550,031 B2 | 1/2017 | Van Sickle et al. |
| 9,561,324 B2 | 2/2017 | Estes |
| 9,600,635 B2 | 3/2017 | Czaja |
| 9,665,689 B2 | 5/2017 | O'Brien et al. |
| 9,675,523 B2 | 6/2017 | Ducatt et al. |
| 9,707,358 B2 | 7/2017 | Eggert et al. |
| 9,730,005 B2 | 8/2017 | Pai |
| 2001/0031072 A1* | 10/2001 | Dobashi ............ G07C 9/253 382/118 |
| 2002/0026332 A1 | 2/2002 | Snowden et al. |
| 2002/0034978 A1 | 3/2002 | Legge et al. |
| 2002/0088825 A1 | 7/2002 | Laverdure |
| 2002/0129816 A1 | 9/2002 | Williams et al. |
| 2002/0165641 A1 | 11/2002 | Manalang et al. |
| 2003/0115082 A1 | 6/2003 | Jacobsen et al. |
| 2003/0216625 A1 | 11/2003 | Phipps |
| 2004/0019502 A1 | 1/2004 | Leaman |
| 2004/0045858 A1 | 3/2004 | Harrold |
| 2004/0073454 A1 | 4/2004 | Urquhart et al. |
| 2004/0077937 A1 | 4/2004 | Yarden |
| 2004/0139000 A1 | 7/2004 | Amos |
| 2004/0158350 A1 | 8/2004 | Ostergaard et al. |
| 2004/0158507 A1 | 8/2004 | Meek et al. |
| 2004/0244794 A1 | 12/2004 | Richards |
| 2004/0249250 A1 | 12/2004 | McGee et al. |
| 2005/0043965 A1 | 2/2005 | Heller et al. |
| 2005/0211768 A1 | 9/2005 | Stillman |
| 2006/0125356 A1 | 6/2006 | Meek, Jr. et al. |
| 2006/0154642 A1 | 7/2006 | Scannell, Jr. |
| 2006/0184524 A1 | 8/2006 | Pollanz |
| 2006/0194075 A1 | 8/2006 | Miyamoto et al. |
| 2006/0204922 A1 | 9/2006 | Anderson et al. |
| 2007/0042488 A1 | 2/2007 | Bornemann |
| 2007/0051072 A1 | 3/2007 | Lai |
| 2007/0104731 A1 | 5/2007 | Kelleher et al. |
| 2007/0185614 A1 | 8/2007 | Bain |
| 2007/0186923 A1* | 8/2007 | Poutiatine ......... A61M 15/0083 128/200.14 |
| 2007/0197978 A1 | 8/2007 | Wortham |
| 2007/0213877 A1 | 9/2007 | Hart et al. |
| 2007/0222554 A1 | 9/2007 | Hart |
| 2007/0261985 A1 | 11/2007 | Allen |
| 2008/0004507 A1 | 1/2008 | Williams et al. |
| 2008/0179387 A1 | 7/2008 | Cantlay et al. |
| 2008/0189173 A1 | 8/2008 | Bakar et al. |
| 2008/0251551 A1 | 10/2008 | Huber et al. |
| 2008/0283542 A1 | 11/2008 | Lanka et al. |
| 2009/0024248 A1 | 1/2009 | Hodson |
| 2009/0055223 A1 | 2/2009 | Jung et al. |
| 2009/0073356 A1 | 3/2009 | Moriyama et al. |
| 2009/0079335 A1 | 3/2009 | Mitsuya et al. |
| 2009/0134368 A1 | 5/2009 | Shibatani et al. |
| 2009/0135120 A1 | 5/2009 | Shibatani |
| 2009/0135349 A1 | 5/2009 | Shibatani et al. |
| 2009/0152514 A1 | 6/2009 | Takiguchi et al. |
| 2009/0152516 A1 | 6/2009 | Shibatani et al. |
| 2009/0152518 A1 | 6/2009 | Takiguchi et al. |
| 2009/0185114 A1 | 7/2009 | Takiguchi |
| 2009/0189128 A1 | 7/2009 | Takiguchi et al. |
| 2009/0230164 A1 | 9/2009 | Freeman |
| 2009/0240528 A1 | 9/2009 | Bluth |
| 2009/0299522 A1 | 12/2009 | Savir et al. |
| 2009/0302048 A1 | 12/2009 | Nobilet et al. |
| 2010/0005445 A1 | 1/2010 | Argue et al. |
| 2010/0016746 A1 | 1/2010 | Hampton et al. |
| 2010/0041056 A1 | 2/2010 | Kinnon et al. |
| 2010/0205009 A1 | 8/2010 | Kostoff |
| 2010/0237338 A1 | 9/2010 | Yamamoto et al. |
| 2010/0250697 A1 | 9/2010 | Hansen et al. |
| 2010/0294927 A1 | 11/2010 | Nelson et al. |
| 2010/0312137 A1 | 12/2010 | Gilmour et al. |
| 2011/0014351 A1 | 1/2011 | Reider et al. |
| 2011/0130635 A1 | 6/2011 | Ross |
| 2011/0173028 A1 | 7/2011 | Bond |
| 2011/0190635 A1 | 8/2011 | Bosler |
| 2011/0270442 A1 | 11/2011 | Conley et al. |
| 2012/0003928 A1 | 1/2012 | Geboers |
| 2012/0066097 A1 | 3/2012 | Amos |
| 2013/0018356 A1 | 1/2013 | Prince |
| 2013/0027206 A1 | 1/2013 | Kosted |
| 2013/0046276 A1 | 2/2013 | Mernoe et al. |
| 2013/0070090 A1 | 3/2013 | Bufalini et al. |
| 2013/0090744 A1 | 4/2013 | Tran |
| 2013/0104284 A1 | 5/2013 | Kantrowitz et al. |
| 2013/0151267 A1 | 6/2013 | Mehdizadeh et al. |
| 2013/0173302 A1 | 7/2013 | Hyde et al. |
| 2013/0231954 A1 | 9/2013 | Bryant |
| 2013/0234855 A1 | 9/2013 | Knighton |
| 2013/0290115 A1 | 10/2013 | Leoni et al. |
| 2013/0297068 A1 | 11/2013 | Marshall |
| 2013/0310664 A1 | 11/2013 | Kozloski et al. |
| 2013/0317835 A1 | 11/2013 | Mathew |
| 2014/0177825 A1 | 6/2014 | Mattsson et al. |

(56) References Cited

U.S. PATENT DOCUMENTS

| | | |
|---|---|---|
| 2014/0277136 A1 | 9/2014 | Stein |
| 2014/0320289 A1 | 10/2014 | Raichman |
| 2014/0346184 A1 | 11/2014 | Bae et al. |
| 2015/0057574 A1 | 2/2015 | Baym et al. |
| 2015/0058041 A1 | 2/2015 | Ervin |
| 2015/0081330 A1 | 3/2015 | Mann et al. |
| 2015/0148943 A1 | 5/2015 | Sullivan |
| 2015/0191268 A1 | 7/2015 | Paz |
| 2015/0191294 A1 | 7/2015 | Paz |
| 2015/0374441 A1 | 12/2015 | Machado et al. |
| 2016/0012445 A1 | 1/2016 | Villa-Real |
| 2016/0066855 A1 | 3/2016 | Hyde et al. |
| 2016/0089303 A1 | 3/2016 | Latorraca et al. |
| 2016/0089491 A1 | 3/2016 | Smith |
| 2016/0158465 A1 | 6/2016 | Coats et al. |
| 2016/0210439 A1 | 7/2016 | Hartlaub et al. |
| 2016/0259183 A1 | 9/2016 | Rayner |
| 2016/0267229 A1 | 9/2016 | High et al. |
| 2016/0283691 A1 | 9/2016 | Ali |
| 2016/0314272 A1 | 10/2016 | Braustein |
| 2016/0331641 A1 | 11/2016 | Longley et al. |
| 2016/0346056 A1 | 12/2016 | Demers et al. |
| 2016/0350500 A1 | 12/2016 | Benja-Athon |
| 2016/0354284 A1 | 12/2016 | Liou et al. |
| 2016/0367188 A1 | 12/2016 | Malik et al. |
| 2016/0367421 A1 | 12/2016 | Ead |
| 2016/0374902 A1 | 12/2016 | Govindasamy |
| 2017/0020785 A1 | 1/2017 | McCullough |
| 2017/0032092 A1 | 2/2017 | Mink et al. |
| 2017/0043896 A1 | 2/2017 | Fernandez |
| 2017/0231870 A1 | 8/2017 | Stachler et al. |

FOREIGN PATENT DOCUMENTS

| | | |
|---|---|---|
| JP | 2006052019 A | 2/2006 |
| WO | 1992020455 A1 | 11/1992 |
| WO | 1996013790 A1 | 5/1996 |
| WO | 199910830 A1 | 3/1999 |
| WO | 2000064754 A1 | 11/2000 |
| WO | 2001067345 A1 | 9/2001 |
| WO | 2001076460 A2 | 10/2001 |
| WO | 2002071955 A2 | 9/2002 |
| WO | 2002095645 A1 | 11/2002 |
| WO | 2003040686 A2 | 5/2003 |
| WO | 2005109119 A1 | 11/2005 |
| WO | 2007070570 A2 | 6/2007 |
| WO | 2009036316 A1 | 3/2009 |
| WO | 2010008377 A1 | 1/2010 |
| WO | 2011002319 A2 | 1/2011 |
| WO | 2011055040 A1 | 5/2011 |
| WO | 2011151056 A1 | 12/2011 |
| WO | 2012040528 A1 | 3/2012 |
| WO | 2012066580 A2 | 5/2012 |
| WO | 2012069896 A1 | 5/2012 |
| WO | 2012098248 A2 | 7/2012 |
| WO | 2012098249 A1 | 7/2012 |
| WO | 2012177524 A1 | 12/2012 |
| WO | 2014059310 A2 | 4/2014 |
| WO | 2014144548 A2 | 9/2014 |
| WO | 2015016375 A1 | 2/2015 |
| WO | 2015113149 A1 | 8/2015 |
| WO | 2015117049 A2 | 8/2015 |
| WO | 2015196293 A1 | 12/2015 |
| WO | 2016030902 A1 | 3/2016 |
| WO | 2016103256 A1 | 6/2016 |
| WO | 2016137186 A1 | 9/2016 |
| WO | 2016155970 A1 | 10/2016 |
| WO | 2016181014 A1 | 11/2016 |
| WO | 2016189497 A1 | 12/2016 |
| WO | 2016196102 A1 | 12/2016 |
| WO | 2017055728 A2 | 4/2017 |

OTHER PUBLICATIONS

Chinese Office Action for CN application 201680069850.4.
Song, et al., "3D Nose: a Novel Biometrics", Journal of Computer-Aided Design & Computer Graphics, vol. 20, No. 1, Jan. 2008.

* cited by examiner

Fig.11

```
Device identifies time to take dose of aerosolized inhalation
                          ↓
         Device informs user, Sound, Visual
                          ↓
         User inserts mouth outlet in mouth
                          ↓
                 User pushes button
                  No ↙         ↘ Yes
                              ↓
              Device photographs underside of nose
                              ↓
                    With or without light
                              ↓
              Device analizes stored picture library to identify user
                   No ↙         ↘ Yes
      Repeat X times              Allows activation
                                        ↓
      Refuse dispense              Activates dispensing
      Give refusal signal                ↓
                              Confirm that dose was taken
      Device informs user          No ↙       ↘ Yes
      to take dose                        Prepare for next dispencing
      Sound, Visual
```

Fig.12

```
Device identifies time to take dose of aerosolized inhalation
                            │
                            ▼
        ┌─► Device informs user, Sound, Visual
        │                   │
        │                   ▼
        │     User inserts mouth outlet in mouth
        │                   │
        │                   ▼
        │         User pushes button
        │           │            │
        │          No           Yes
        │           │            │
        └───────────┘            ▼
                      ┌─► Device photographs
                      │         mouth
                      │           │
                      │           ▼
                      │   With or without light
                      │           │
                      │           ▼
                      │   Device recognizes that it
             Repeat   │        is in mouth
             X times  │       │          │
               │      │      No         Yes
               │      └───────┘          │
               ▼                         ▼
       Refuse dispense              Allows activation
       Give refusal                       │
         signal                           ▼
                                   Activates dispencing
                                          │
                                          ▼
       Device informs   ──────►   Confirm that dose
       user to take dose               was taken
       Sound, Visual              No │          │ Yes
             ▲                       │          │
             └───────────────────────┘          ▼
                                         Prepare for next
                                           dispencing
```

IMAGE RECOGNITION-BASED DOSAGE FORM DISPENSERS

RELATED APPLICATIONS

This application is a United States National Phase entry of International Application No. PCT/IL2016/051109, filed Oct. 13, 2016, which claims the benefit of U.S. Provisional Patent Application No. 62/406,012, filed Oct. 10, 2016, and U.S. Provisional Patent Application No. 62/241,808, filed Oct. 15, 2015. The entire contents of each of the foregoing applications are hereby incorporated by reference herein.

FIELD OF THE INVENTION

The present invention generally relates to image recognition-based dosage form dispensers, which, inter alia are configured to dispense medications to authorized individuals.

BACKGROUND OF THE INVENTION

A major problem in hospitals and nursing facilities, where various orally formulated medications are dispensed on a regular basis, is that same are manually conveyed by medical personnel to a patient who then manually retrieves and swallows the medication. Unfortunately, many patients receiving medication are groggy, shaky or infirm. During the handling of the pills, the patient may drop the pills, which will result in their becoming contaminated or even lost.

Another problem in hospitals, and in general, is with the control of the distribution of narcotic pain killers, where patients are known to palm the same in order to transfer and/or sell the pill to an unauthorized user.

Still another issue is the lack of ability to provide a means for dispensing controlled medications in a mobile, home care setting, i.e. without need for authorized medical personnel to dispense same.

Traditional means of addressing this issue was to provide the medication, in the form, e.g. of pills, tablets, capsules, caplets, gel-caps, pellets, sprays and inhalers, etc., have traditionally been provided in the form of a disposable plastic container with a childproof cap. When physicians prescribe medications, they typically advise the patients of proper precautions to follow during the medication administration, such as storing the medications correctly to optimally preserve them, to take the medications at appropriate times and quantities, to continue taking the medications for the full prescribed regimen, even if the patient feels better, etc.

Unfortunately, patients frequently exhibit poor patient compliance in properly following through a particular drug regimen. Some factors associated with poor compliance include memory loss and other cognitive dysfunctions, poor patient motivation, attenuation of special senses, poor eyesight, lack of patient education, etc.

A variety of products and techniques for reminding patients during medication regimens are known, and are generally cost prohibitive. Therefore, a need exists for an electronic pill dispenser that is configured to remind and dispense medications to authorized individuals at appropriate times and that is economical and convenient. In addition, a particular need exists for an electronic pill dispenser configured to remind and dispense pills, capsules, pellets, tablets, or the like having any particular size and shape.

Some available solutions include containers for storing and dispensing pills, which are manually operable, and dispense the oral dosage form contained therein in the user's hand or otherwise necessitate the user manually handling the oral dosage form, as well. Other known devices may obviate the need for user handling the dosage form, e.g. by inhalation, but these devices typically deliver fine powders, or if they deliver a solid dosage form, the design is quite complex and not broadly applicable nor user friendly.

There remains a need for a more automated, yet regulated oral solid dosage form dispenser without the above-noted limitations.

SUMMARY

This invention provides a partial facial recognition-based, oral dosage or aerosolized or inhalation form dispensers and methods of use of same.

In another aspect, this invention provides for an image recognition-based, dosage form dispenser and methods of use of same.

In some embodiments, the image recognition is derived, in whole or in part, from images taken within the oral cavity of a user, thereby relying on same for delivery of a dosage form.

In some embodiments, the image recognition is derived, in whole or in part, from images taken within the oral cavity of a user, that analyze the specific dosage form being ingested/taken up by the user.

In some embodiments, this invention provides a dosage form dispenser relying on both partial facial recognition and partial recognition of images taken within an oral cavity of a subject, for dispensing the dosage form.

In some aspects, the dosage form dispensers comprise a casing, which can be engaged by the mouth of a specific user and which casing further contains a controllable dosage form dispenser, for which the dosage form only becomes accessible to the specific user after specific authentication is achieved.

In some aspects, authentication relies on data obtained from at least one camera. The camera or cameras which constitute part of the systems of this invention capture(s) a field of view of, in some embodiments, at least a portion of a base view of a nose of a subject, and in other embodiments, at least a portion of a view of an oral cavity of a subject, and in some embodiments, images from both the portion of a base view of a nose of a subject and a portion of a view of an oral cavity of a subject are captured, and then the system compares such captured images to a user standard, relaying authentication when a suitable match is obtained.

This invention provides, in one embodiment, a dosage form dispenser, comprising:
  a casing comprising a first portion adapted for insertion within an oral cavity of a subject and a second portion adapted to encase a dosage form dispensing mechanism located therewithin;
  at least one camera positioned on said second portion of said casing, further positioned to capture a field of view of a portion of a face of a subject, wherein said field of view comprises at least a portion of a base view of the nose of said subject;
  a dosage form dispensing mechanism;
  a microprocessor and associated memory for processing and storing user authentication information, comparing images relayed from said at least one camera to at least one stored user standard and providing authentication when a match is established; and an interface connected to said dispensing mechanism, which promotes dispensing said dosage form when said authentication has been obtained.

This invention provides, in some embodiments, a dosage form dispenser, comprising:
- a casing comprising a first portion adapted for insertion within an oral cavity of a subject and a second portion adapted to encase a dosage form dispensing mechanism located therewithin;
- at least one camera positioned on said first portion of said casing, further positioned to capture a field of view of a portion of an oral cavity of a subject, wherein said field of view comprises at least a portion of a top view or a base view of an oral cavity of a subject, or a combination thereof;
- a dosage form dispensing mechanism;
- a microprocessor and associated memory for processing and storing user authentication information, comparing images relayed from said at least one camera to at least one stored user standard and providing authentication when a match is established; and
- an interface connected to said dispensing mechanism, which promotes dispensing said dosage form when said authentication has been obtained.

This invention provides, in some embodiments, a method for dispensing a dosage form in a manner directly within an oral cavity of a subject in need thereof, said method comprising:
- Inserting a first portion of a casing of a dosage form dispenser adapted for insertion within an oral cavity of said subject, wherein said dosage form dispenser further comprises
  - a second portion of said casing;
  - at least one camera positioned on said second portion, further positioned to capture a field of view of a portion of a face of a subject, wherein said field of view comprises at least a portion of a base view of the nose of said subject;
  - a dosage form dispensing mechanism;
  - a microprocessor and associated memory for processing and storing user authentication information, comparing images relayed from said at least one camera to at least one stored user standard and providing authentication when a match is established; and
  - an interface connected to said dispensing mechanism, which promotes dispensing said dosage form when said authentication has been obtained;
- activating said at least one camera to capture a field of view of a portion of a face of said subject;
- activating said microprocessor to compare at least one image related from said at least one camera to at least one stored user standard and providing authentication when a match therebetween is established; and
- activating said interface to promote dispensing said dosage form when said authentication has been obtained.

This invention provides, in some embodiments, a method for dispensing a dosage form directly within an oral cavity of a subject in need thereof, said method comprising:
- inserting a first portion of a casing of a dosage form dispenser adapted for insertion within an oral cavity of said subject, wherein said dosage form dispenser further comprises
  - a second portion of said casing;
  - at least one camera positioned on said first portion, further positioned to capture a field of view of a portion of an oral cavity of a subject, wherein said field of view comprises at least a portion of a top view or a base view of an oral cavity of a subject, or a combination thereof;
  - a dosage form dispensing mechanism;
  - a microprocessor and associated memory for processing and storing user authentication information, comparing images relayed from said at least one camera to at least one stored user standard and providing authentication when a match is established; and
  - an interface connected to said dispensing mechanism, which promotes dispensing said dosage form when said authentication has been obtained;
- activating said at least one camera to capture a field of view of a portion of a face of said subject;
- activating said microprocessor to compare at least one image related from said at least one camera to at least one stored user standard and providing authentication when a match therebetween is established; and
- activating said interface to promote dispensing said dosage form when said authentication has been obtained.

BRIEF DESCRIPTION OF THE DRAWINGS

FIG. 11 schematically depicts an embodied protocol for using and authenticating the dispensing device for delivery of an aerosol of this invention.

FIG. 12 schematically depicts another embodied protocol for using and authenticating the dispensing device for delivery of an aerosol of this invention.

DETAILED DESCRIPTION OF THE INVENTION

Figure 1:
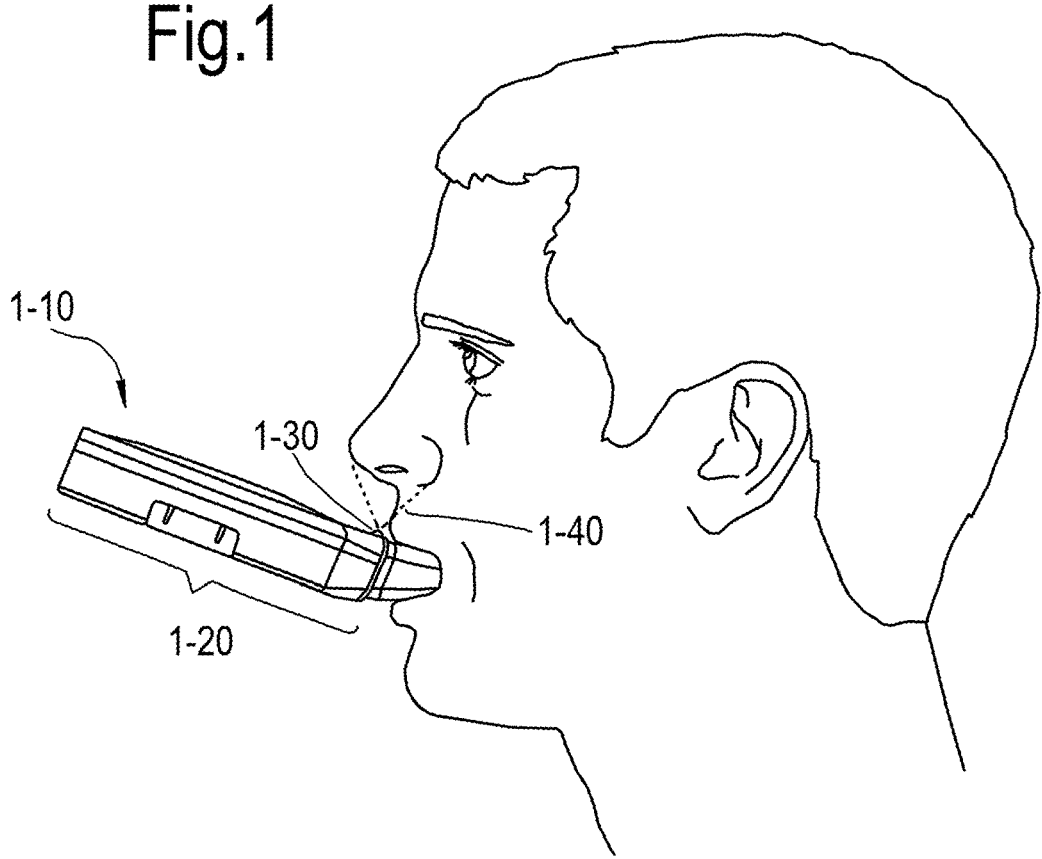
FIG. 1 schematically depicts an embodied dosage form dispenser of this invention, showing potential placement of a camera 1-30 positioned on the second portion of the casing 1-20, further positioned to capture a field of view of a portion of a face of a subject, wherein said field of view comprises at least a portion of a base view of the nose of said subject 1-40.

This invention provides a partial facial recognition-based, secured dosage form dispenser. The dosage form dispensers of this invention will comprise a casing, which can be engaged by the mouth of a specific user and which casing further contains a controllable oral dosage form dispenser, for which the oral dosage form only becomes accessible to the specific user after specific authentication is achieved.

Authentication relies on data obtained from the at least one camera contained on or within the dosage form dispenser, which camera captures a field of view of at least a portion of a base view of a nose of a subject, which field of view/captured image is then compared to a user standard, relaying authentication when a suitable match is obtained.

One embodied advantage of the dispensers of this invention is the authentication reliance on a field of view of at least a portion of a base view of a nose of a subject, which is obtained while a portion of the dispenser is located within the mouth of a user, such that authentication can occur while the user is poised for direct delivery of the regulated dosage form into his or her mouth.

In some embodiments, the dispensers of this invention promote regulated delivery of an oral dosage form, and in some embodiments, the dispensers of this invention promote regulated delivery of an aerosol dosage form, or in some embodiments, dispensers of this invention promote regulated delivery of a dosage form suitable for inhalation, for example, a powdered dosage form that can be inspired.

In some embodiments, reference to an oral dosage form dispenser is just as applicable in terms of dispensing a dosage form that enters the oral cavity for inhalation, e.g. aerosol or powder for inhalation purposes, etc. and is to be considered as part of this invention.

In another embodiment, another advantage of the dispensers of this invention is the authentication reliance on a field of view of at least a portion of a view of an oral cavity of a subject, which is obtained while a portion of the dispenser is located within the mouth of a user, such that authentication can occur while the user is poised for direct delivery of the regulated dosage form into his or her mouth and/or facilitates confirmation of depositing the dosage form within the mouth of the subject.

In still another embodiment, the dispensers of this invention comprise cameras facilitating views of both a base view of a nose of a subject and field of view of at least a portion of a view of an oral cavity of a subject, and thereby providing the advantages associated with both, as described hereinabove.

According to these aspect, the dispenser of this invention provides sufficient accuracy in authentication, during real-time use, providing an added security benefit in terms of conjoining authentication with most proximal delivery of the dosage form.

In some aspects, the oral dosage form dispenser casing is tamper-proof, and essentially inaccessible in the absence of authentication, which enables proper dispensing of any oral dosage forms contained therein.

In addition to being tamper proof, as will be appreciated by the skilled artisan, the dispenser casing will be formed as a receptacle for storing and dispensing any size of dosage form, or contain any dosage form in discrete compartments, or multiple dosage forms in discrete compartments, or in some embodiments in blister packages and further described herein. In some aspects, such casing may be made from durable material, such as flexible plastic, rubber, or the like, and while in some embodiments, such casing is illustrated as a rounded container, such dispenser may be configured in any shape as desired. In some aspects, the casing may be clear, transparent, and/or translucent, or may be opaque and be provided with any type of color or combination of colors, or have decorative symbols or indicia provided thereon.

In some embodiments, the dosage form dispensers of this invention are to be considered "secured", which in some embodiments, refers to the fact that any medication located therein cannot be accessed in the absence of appropriate authentication so that such medication is secured from unauthorized use.

In some aspects, the term "secured" and grammatical forms thereof refers to a means of preventing an unauthorized user access, or access even by an authorized user and a non-authorized time or interval.

In some aspects, the oral dosage form dispenser accommodates dispensing of oral dosage forms provided in a blister pack, which blister pack is then contained within the secured casing.

In some aspects, the oral dosage form dispenser accommodates dispensing of oral dosage forms provided as individual dosage forms, located within discrete advancing compartments in the dispenser, facilitating specific dispensing of multiple forms in a secured manner.

This invention provides, in one embodiment, a dosage form dispenser, comprising:
  a casing comprising a first portion adapted for insertion within an oral cavity of a subject and a second portion adapted to encase a dosage form dispensing mechanism located therewithin;
  at least one camera positioned on said second portion of said casing, further positioned to capture a field of view of a portion of a face of a subject, wherein said field of view comprises at least a portion of a base view of the nose of said subject;
  a dosage form dispensing mechanism;

a microprocessor and associated memory for processing and storing user authentication information, comparing images relayed from said at least one camera to at least one stored user standard and providing authentication when a match is established; and an interface connected to said dispensing mechanism. which promotes dispensing said dosage form when said authentication has been obtained.

In some aspects, the casing is an enclosure, which promotes proper dispensing of oral dosage forms within a mouth of a user and providing in some aspects, a tamper proof container.

In some aspects, the dispensers of this invention further comprise a device for analyzing spectral characteristics, for example, in some embodiments, a spectrophotometer, or spectra analyzer, such as, for example, NIR spectroscopy, and others, as will be appreciated by the skilled artisan.

In some aspects, such spectral analyzers may be miniaturized, and present on the device, or in some embodiments, such spectral analyzers may be in devices in communication with the dispensers of this invention, such as for example, in use in a mobile phone or other mobile device, whereby communication between the device containing the spectral analyzer is promoted with the dispensers of this invention, and upon authentication being achieved via the spectral analyzer, a relay to the dispenser is provided, to participate in the authentication protocol of the dispensers of this invention.

In some embodiments, the dispenser may also analyze the dosage form, in terms of its spectral properties or others, to ensure the appropriate dosage form is being administered to the subject.

In some embodiments, another aspect of the authentication procedure may include analysis of the saliva of the subject, when the dispenser is placed in the mouth of the subject. In some aspects, such analysis may confirm proper placement within the mouth of the user, for example, by measuring the pH of the environment, capacitance, humidity, carbon dioxide concentration, temperature, or presence of particular enzymes, or other indicators, as will be appreciated by the skilled artisan.

In some aspects, the sensor may be further optimized to detect a particular characteristic present uniquely in the saliva of the user, providing an added safety/authentication characteristic.

In some embodiments, the dosage form dispensing mechanism is modular, comprising at least one oral dosage form containing cassette which can be sequentially advanced within the dispenser. In some aspects, the cassette may be disposable. In some aspects, the cassette may be re-fillable.

According to this aspect, in some embodiments, the modular dispensers of this invention may be refilled with appropriate dosage forms by an authorized service provider only, e.g. a pharmacist, or medical personnel, who may utilize a special apparatus, or key, to remove the dosage form containing cassette.

In some embodiments, the at least one dosage form is contained within a blister package, which comprises a covered cavity bounded by a backing containing a dosage form therewithin.

In some embodiments, the blister package comprises an array of dosage forms.

In some embodiments, the array comprises at least one linear column of dosage forms or at least one circular distribution of dosage forms.

In some aspects, the cassette is specifically designed to contain standard blister packages as known to the skilled artisan.

In some embodiments, one or more dosage forms may be contained within a single blister.

In some embodiments, one or more dosage forms may be contained within at least one enclosed compartment within the dispensing mechanism.

In some embodiments, the dosage form dispenser further comprises an outlet connected to said conveyor and configured for engagement and selective actuation by the mouth of a user, promoting egress of said at least one dosage form from said dosage form dispensing mechanism into the oral cavity of said subject.

In some embodiments, the dispenser further comprises an outlet configured for engagement and selective actuation by the mouth of a user, promoting egress of said at least one dosage form from said dosage form dispensing mechanism into the oral cavity of said subject.

It will be appreciated by the skilled artisan that dispensing a dosage form from the dispensers of this invention cannot occur in the absence of a properly executed authentication protocol as herein described.

In some embodiments, the dispenser further comprises a selective depilling mechanism, whose activity can only be engaged following proper authentication.

In some embodiments, when the dispenser contains a blister pack therewithin, the dispenser further comprises a selective depilling mechanism comprising a double action depilling mechanism.

In some embodiments, the selective depilling mechanism comprises a double action depilling mechanism, comprising a first pusher, sized and adapted to engage a top surface of said covered cavity and to exert a first sufficient force thereagainst so as to push said dosage form contained therein against its respective bounding backing, and a second pusher sized and adapted to more forcibly engage said top surface of said covered cavity and to exert a second sufficient force thereagainst so as to expel said dosage form from said blister.

In some aspects, the various depilling means as described herein and as known in the art, cannot be engaged if proper authentication has not been obtained.

The dosage form dispensers have an authentication process, which makes use of information obtained by means of a camera located thereon or therein.

The camera is positioned on the second portion of the casing of the dispenser. In some aspects, the reference to the camera being "positioned on" does not preclude the option of the camera being incorporated within the casing. It will be appreciated and understood that the camera may be placed within or on the second portion of the casing in any manner that facilitates its proper use to capture a field of view of a portion of a face which field of view comprises at least a portion of a base view of the nose of the subject.

Figure 2:
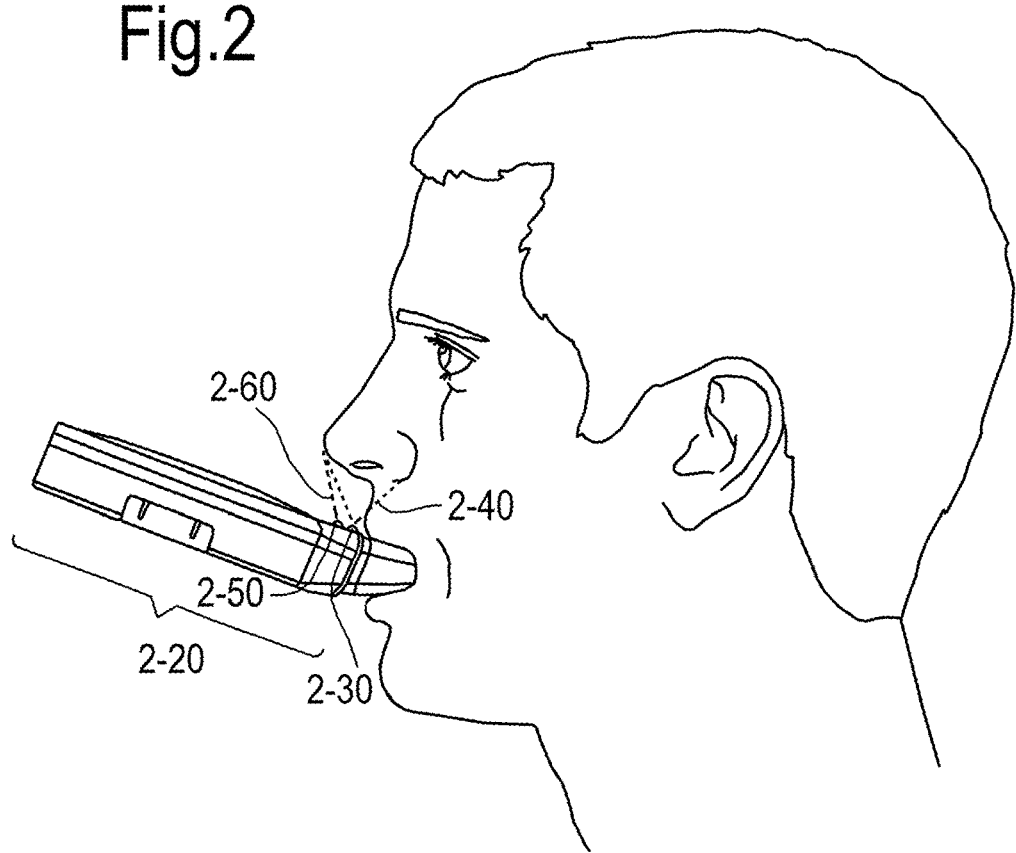
FIG. 2 schematically depicts an embodied dosage form dispenser of this invention, showing potential placement of two cameras 2-30, 2-50 positioned on the second portion of the casing 2-20, further positioned to capture a field of view of a portion of a face of a subject, wherein said field of view comprises at least a portion of a base view of the nose of said subject 2-40, 2-60.

Referring to FIG. 1, an embodied dosage form dispenser 1-10 is depicted. A camera 1-30 is positioned on the second portion 1-20, and a field of view 1-40 can then be captured by the camera, which field of view encompasses at least a portion of a face of the user, including at least a portion of a base view of the nose of the user. FIG. 2 provides another embodied dosage form dispenser, which in this depicted aspect has more than one camera, here two cameras 1-30 and 1-50, respectively, which in turn capture different fields of view, 1-40 and 1-60, respectively, each field of view encompassing at least a portion of a face of the user, including at least a portion of a base view of the nose of the user.

Figure 7:
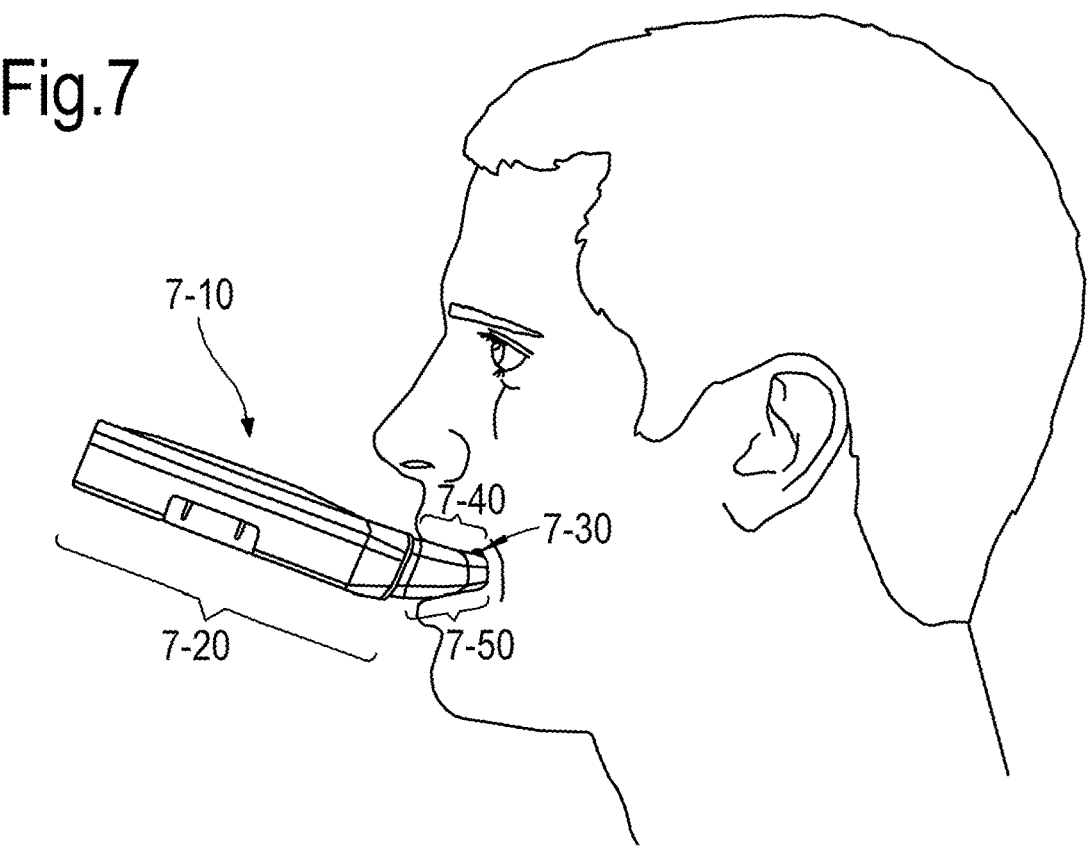
FIG. 7 schematically depicts an embodied dosage form dispenser 7-10 of this invention, showing potential placement of a camera 7-30 positioned on the first portion of the casing 7-50, further positioned to capture a field of view of a portion of an oral cavity of a subject, and positioning of the camera facilitates image collection of an apical or upper view 7-40 of the oral cavity.
Figure 8:
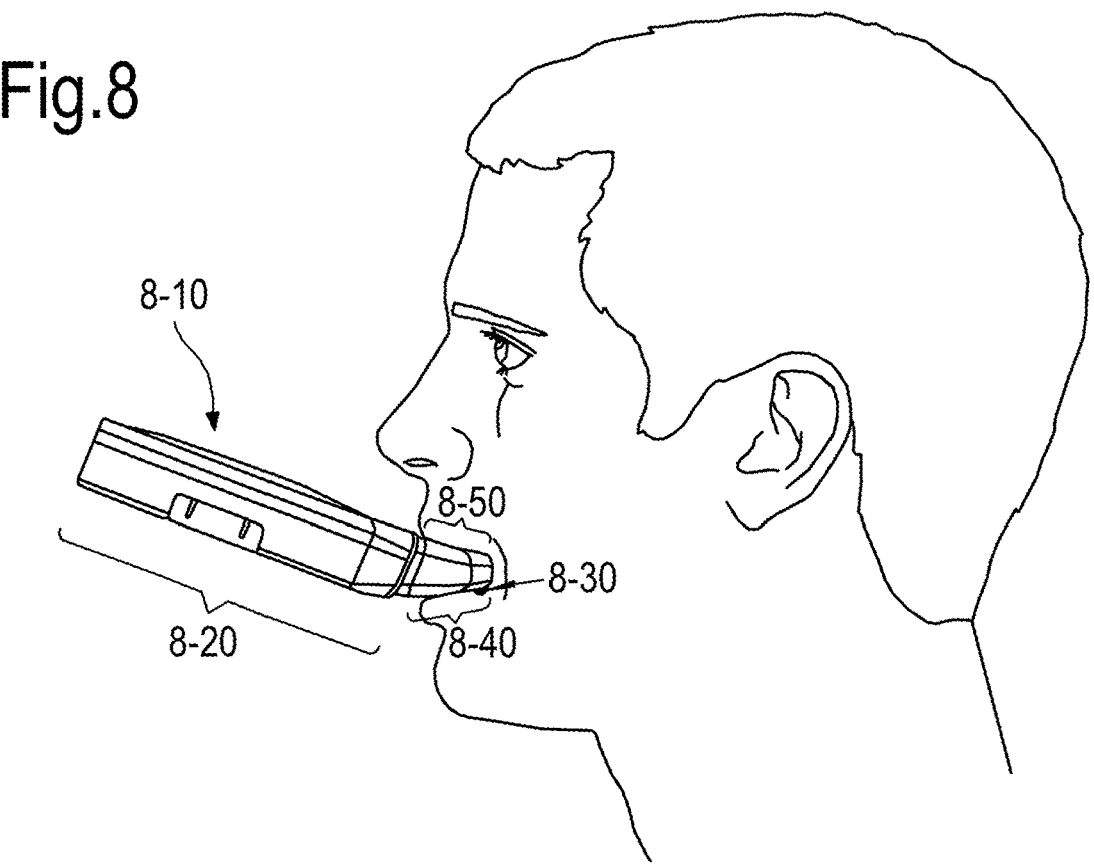
FIG. 8 schematically depicts an embodied dosage form dispenser 8-10 of this invention, showing potential placement of a camera 8-30 positioned on the first portion of the casing 8-50, further positioned to capture a field of view of a portion of an oral cavity of a subject, and positioning of the camera facilitates image collection of a basal or lower view 8-40 of the oral cavity.

Referring to FIG. 7, an embodied dosage form dispenser 7-10 is depicted. A camera 7-30 is positioned on the first portion 7-50, and a field of view 7-40 can then be captured by the camera, which field of view encompasses at least a portion of the upper area of the oral cavity of the user. FIG. 8 provides another embodied dosage form dispenser, which in this depicted aspect has a camera 8-30 positioned on the first portion 8-50, and a field of view 8-40 can then be captured by the camera, which field of view encompasses at least a portion of the lower or basal area of the oral cavity of the user.

The skilled artisan will readily appreciate that the fields of view captured by more than one camera may be overlapping fields of view, in some aspects, and may further refine a captured image, to ensure greater accuracy for user authentication purposes.

In some aspects, the second portion which is adapted to encase a dosage form dispensing mechanism is further angled with respect to the first portion and in some embodiments, such angling may optionally be further adjustable, to optimize the field of view capture, and/or ultimately to optimize authentication.

According to this aspect, such angling of the second portion, in some aspects, allows for optimal positioning of at least one camera in order to capture a clearer field of view of the portion of the subject's face. In some embodiments, positioning of the at least one camera is proximal to the first portion of the casing.

In some embodiments, the casing comprises two or three cameras positioned on the second portion of the casing and in some embodiments, the cameras may be proximal to the first portion of the casing.

Figure 3:
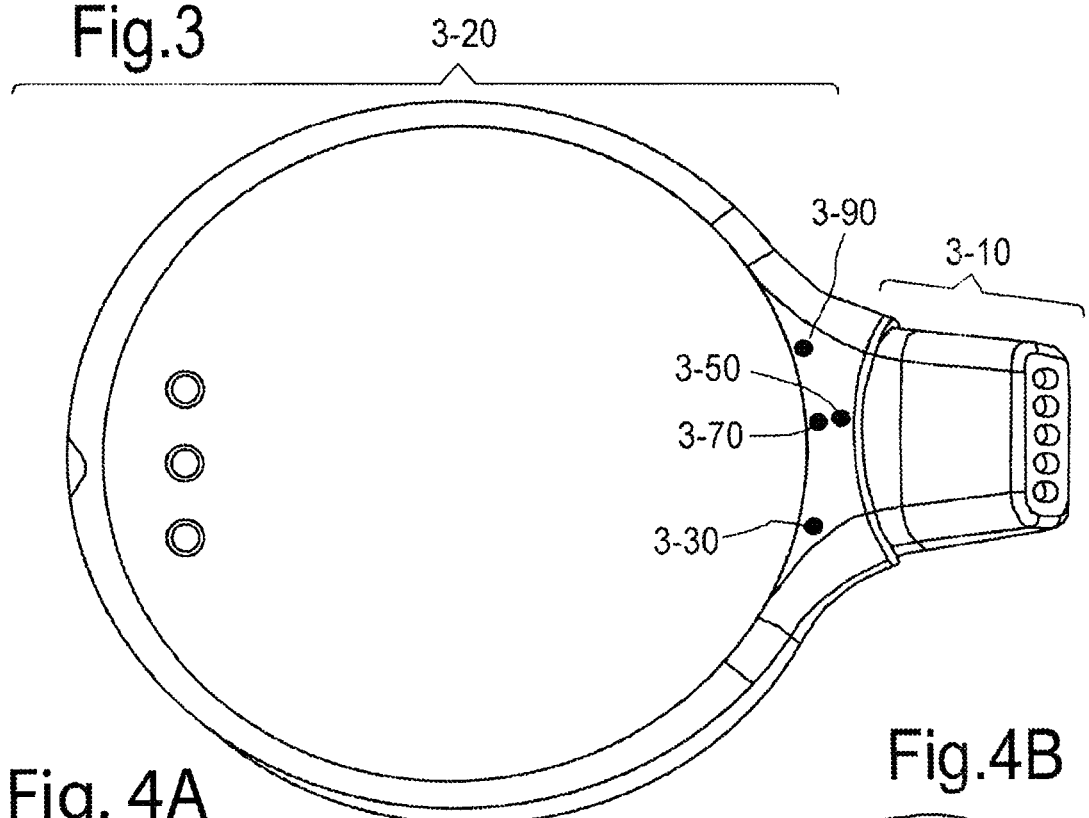
FIG. 3 depicts an embodied dosage form dispenser of this invention, showing potential placement of various cameras 3-30, 3-50, 3-70, 3-90 positioned on the second portion of the casing 3-20, and showing the first portion of the casing 3-10.

Referring to FIG. 3, an embodied dosage form dispenser of the invention is schematically depicted with only certain external elements depicted. According to this aspect, and in some embodiments, the first portion 3-10 and second portion 3-20 are shown, and the figure depicts the angling of the second portion with respect to the first, and the positioning of multiple cameras 3-30, 3-50, 3-70 and 3-90 on the dosage form dispenser, or in some embodiments, one or more of the thus designated cameras may instead be a light source, as herein described.

Figure 9:
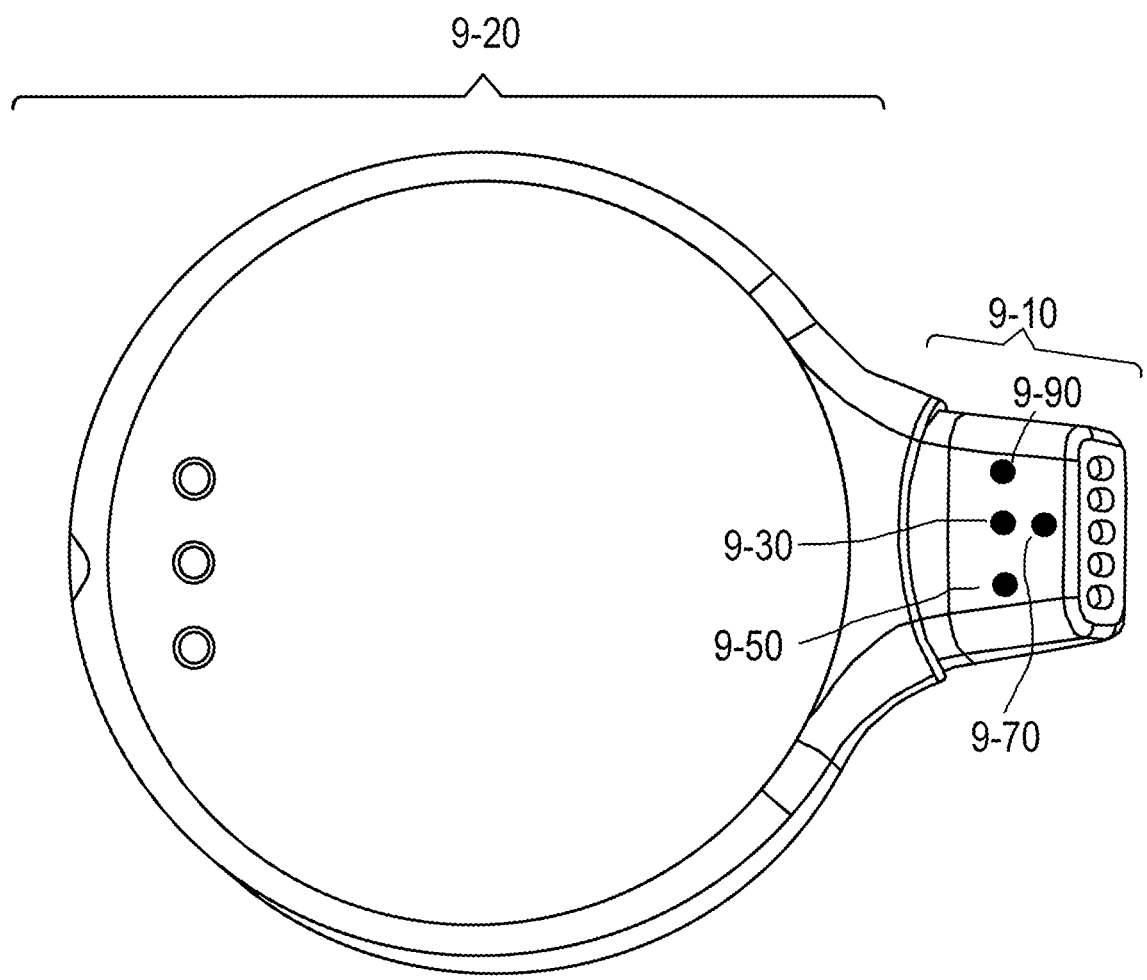
FIG. 9 depicts an embodied dosage form dispenser of this invention, showing potential placement of various cameras 9-30, 9-50, 9-70, 9-90 positioned on the first portion of the casing 9-10, and showing the second portion of the casing 9-20.

Similarly, referring to FIG. 9, the potential placement of various cameras 9-30, 9-50, 9-70, 9-90 positioned on the first portion of the casing 9-10, is depicted, and similarly, one or more of the elements designated as cameras (9-30, 9-50, 9-70, 9-90) could readily be understood to represent a light source, as described herein.

In some embodiments, the casing further comprises at least one light source positioned on the second portion or first portion of the device, as described.

According to this aspect, and in some embodiments, the light source facilitates improved image capture from said at least one camera, improved user experience with said dispenser or a combination thereof. Similarly, in some embodiments, one or more light sources may be placed on the second portion to improve the quality of the captured image information.

In some embodiments, the at least one camera has a zoom feature.

In some embodiments, the dispenser further comprises a real-time clock for generating time signals which signals are processed and compared to a pre-set time schedule and can override activation of positioning of said at least one dosage form or activation of said depilling mechanism if the time signals processed do not match said pre-set time schedule.

In some embodiments, the dispenser further comprises a user alert indicator operationally coupled to a real-time clock, which alerts the subject about a scheduled time for dispensing said dosage form.

In some embodiments, processing said user authentication information may comprise rotating or skewing images relayed from said at least one camera prior to or while comparing same to said at least one stored user standard.

Figure 4A:
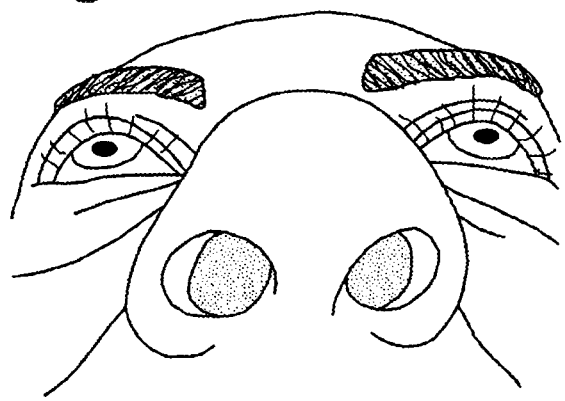
FIG. 4A and FIG. 4C, respectively, show photographs of two subjects, providing a field of view of a portion of the face of each subject, where the field of view comprises at least a portion of a base view of the nose of each subject.
Figure 4B:
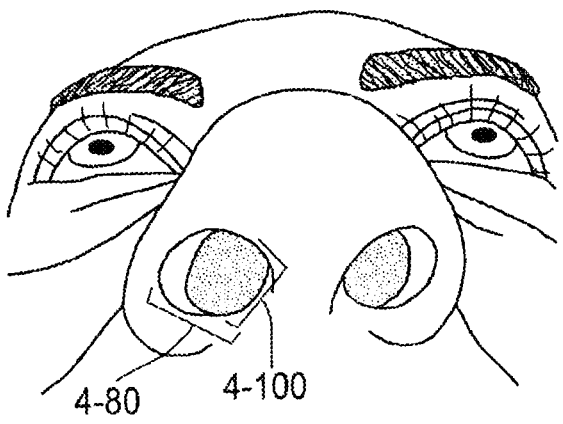
FIG. 4B and FIG. 4D schematically depict the same views, showing that such field of views provide sufficient identifying information to serve as the basis for authentifying information, for example, as the differences from such views are obvious, e.g. the horizontal and vertical sizing of the nostrils, 4-80 and 4-100, as compared to 4-90 and 4-110, respectively.
Figure 4C:
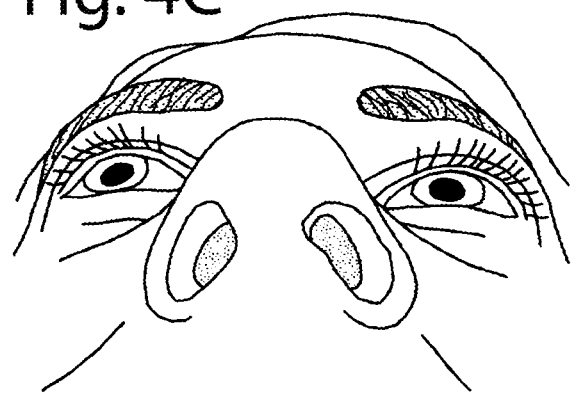
Figure 4D:
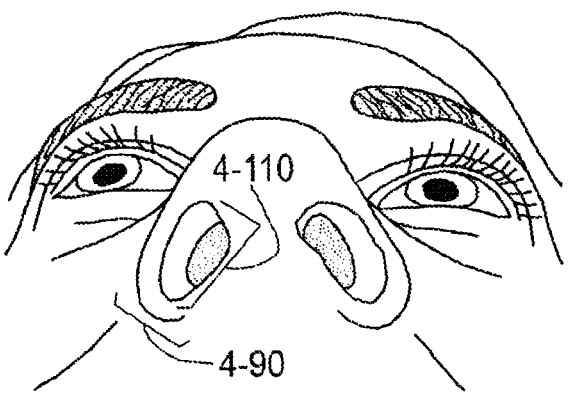

For example and referring to FIGS. 4A and 4C, as is evident, the captured images represent two different users, a male (FIG. 4A) and female (FIG. 4C). If a dosage form dispenser was specifically calibrated for use by the male subject of FIG. 4A, then use of same by the user in FIG. 4C would fail authentication. In some aspects, it may be beneficial to render the acquired image in a schematic, flattened depiction, as in FIGS. 4B and 4D. According to this aspect, and in some embodiments, part of the authentication protocol may be to specifically measure the horizontal and vertical diameters across a nostril of the user, as part of the authentication procedure. As seen in FIGS. 4B and 4D, such horizontal measurements 4-80 versus 4-90 would yield a smaller value from FIG. 4D than the standard depicted in FIG. 4B, and similarly, the vertical measurements, 4-100 versus 4-110, would yield a larger value from FIG. 4D than the standard depicted in FIG. 4B. According to this aspect, the authentication protocol in use in the embodied dosage form dispenser, if used by the user in FIG. 4C, when the dispenser was calibrated for the user in FIG. 4A would provide a failure notice and the dosage form dispenser would not dispense the oral dosage form contained therein.

Figure 4E:
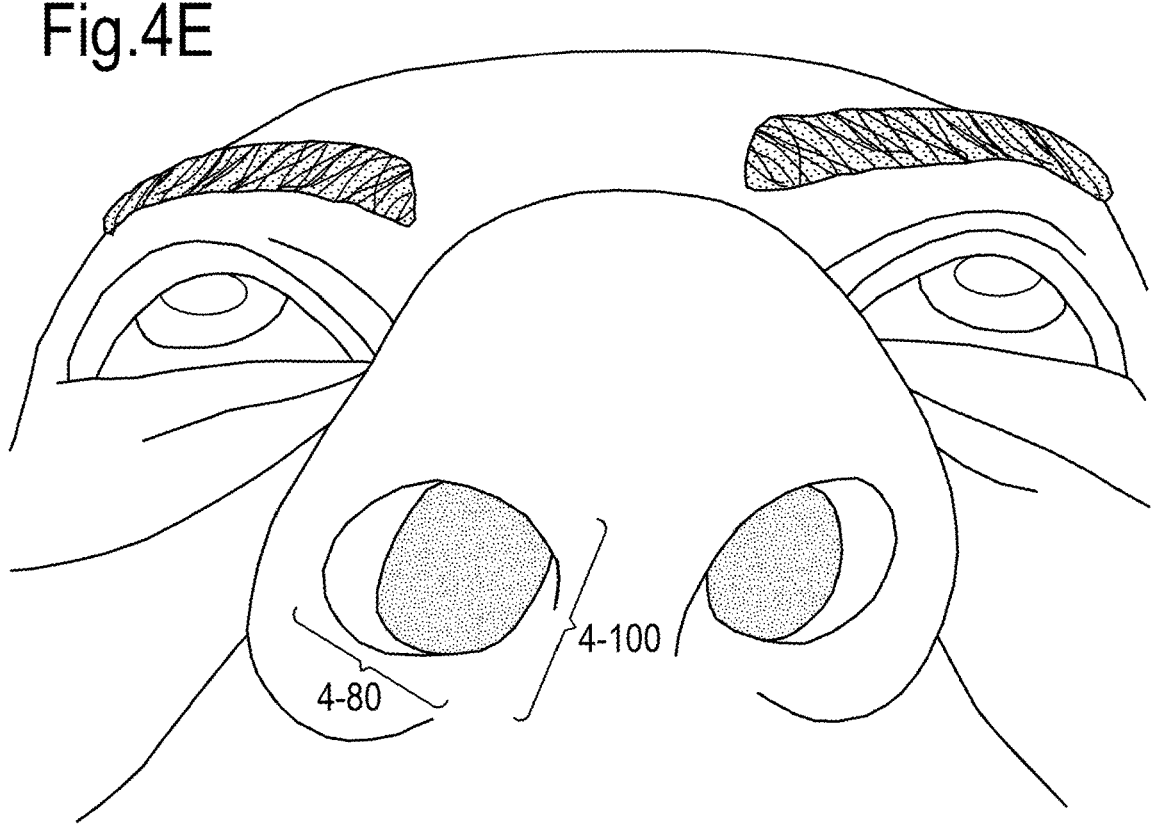
FIG. 4E and FIG. 4F show that such views are still obviously different, even when two subjects of similar age and ethnicity are compared e.g. the horizontal and vertical sizing of the nostrils, 4-80 and 4-100, as compared to 4-90 and 4-110, respectively, and that glasses being worn on a subject (for example, as in FIG. 4F) does not obscure same.
Figure 4F:
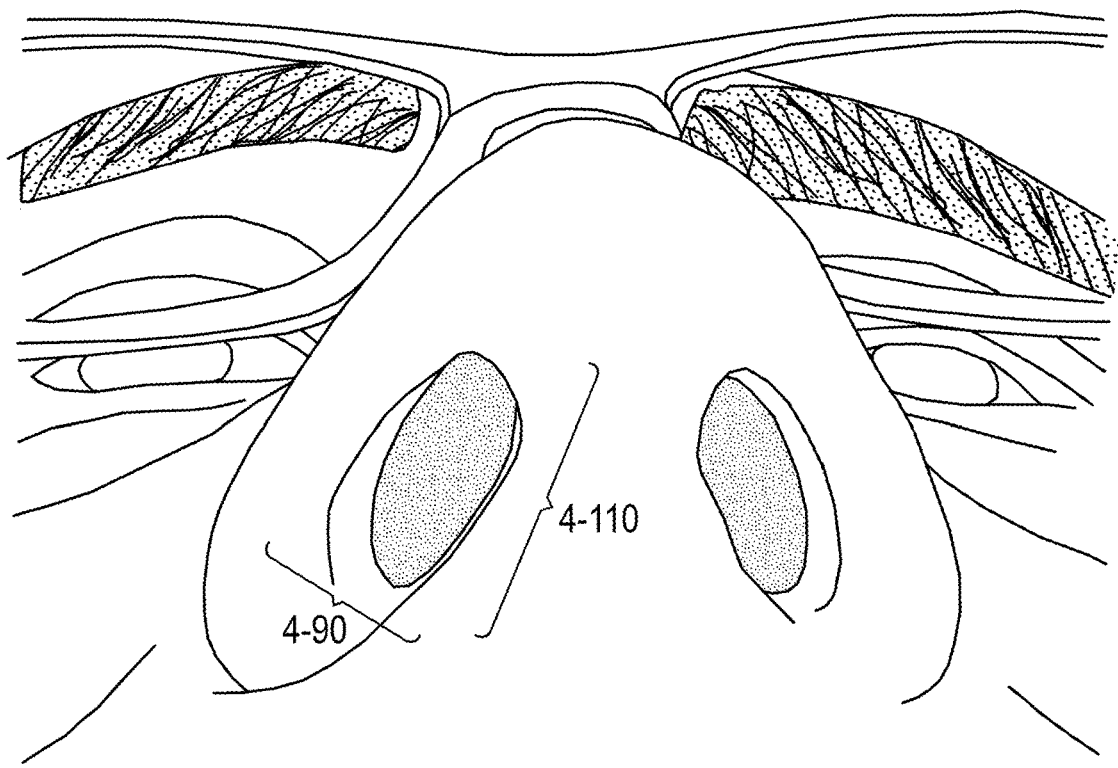

Referring to FIGS. 4E and 4F, the calibration of the dosage form dispenser is specific enough to, for example, distinguish between two users with a similar overall appearance. Authentication based on captured fields of view of a portion of a face of a subject, comprising as little as a portion of a base view of the nose of said subject is sufficient, in some aspects to serve as a robust foundation for authentication purposes. For example, comparing FIG. 4E to 4F, part of the authentication protocol may be to specifically measure the horizontal and vertical diameters across a nostril of the user, as part of the authentication procedure as conducted for FIGS. 4B and 4D. Such horizontal measurements 4-80 versus 4-90 would yield a smaller value from FIG. 4F than the standard depicted in FIG. 4E, and similarly, the vertical measurements, 4-100 versus 4-110, would yield a larger value from FIG. 4F than the standard depicted in FIG. 4E. According to this aspect, the authentication protocol in use in the embodied dosage form dispenser, if used by the user in FIG. 4F, when the dispenser was calibrated for the user in FIG. 4E would provide a failure notice and the dosage form dispenser would not dispense the oral dosage form contained therein.

It will be appreciated that collection of the captured images and comparison versus a standard will rely on relative matches with the measured parameters, and that such comparison need not be absolute, since for example, scaling may be a further factor in collection of same.

Figure 5:
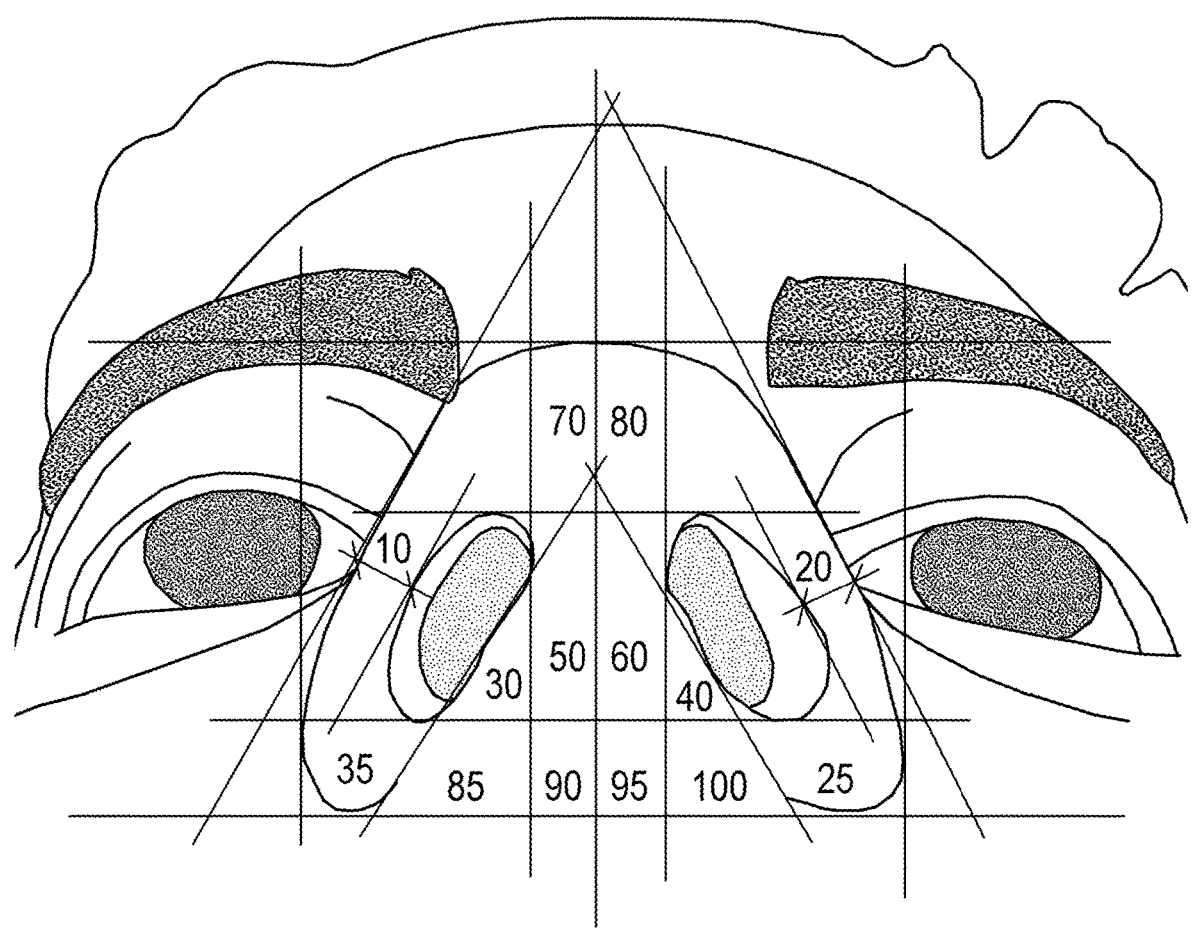
FIG. 5 schematically depicts a variety of parameters that can be compared from different fields of view captured from a user using the device of the subject invention.

Referring to FIG. 5, as will be appreciated, after collection of an image of even such minimal view such as a portion of a base view of the nose of said subject, is sufficient to provide a robust means of distinguishing between authorized users versus unauthorized users, i.e. comparing a captured image of a user with identifying features that match a standard generated for the user, versus captured images that do not match the standard.

In some embodiments, the stored user standard may be a compilation of user images captured and stored over time. In some embodiments, as will be appreciated by the skilled artisan, the stored user standard can be a compilation of specific data point values obtained from the analysis of such user images, as well.

In some embodiments, the stored user standard may comprise a weighted determination introducing a bias in favor of more recently stored images.

In some embodiments, processing said user authentication information may comprise using aging algorithms.

In some embodiments, processing said user authentication information may comprise establishing at least a two-identifier point match between features identified from said portion of a base view of the nose of said subject as compared to said stored user standard.

In some embodiments, processing said user authentication information may comprise establishing a three-identifier point to ten-identifier point match between features identified from said portion of a base view of the nose of said subject as compared to said stored user standard.

As described herein, such match identification may well rely on relative measurements or ratios between relative measurements as opposed to absolute differences in values, and the relative measurements are sufficiently accurate for authentication purposes.

In some embodiments, the identifier point is a measurement comprising a distance between an outer nare surface and outer nostril boundary, a distance between an outer nare surface and inner nostril boundary; a distance between an outer nostril boundary and inner nostril boundary; a distance between a first outer nare surface and a second outer nare surface; a distance between a first outer nare surface and a nasal midline versus a distance between a second outer nare surface and said nasal midline; a distance between a first outer nostril and a nasal midline versus a distance between a second outer nostril and said nasal midline; a distance between a first inner nostril and a nasal midline versus a distance between a second inner nostril and said nasal midline; an angle formed between a parallel plane to a first outer nare surface and a plane parallel to a nasal midline versus a distance between a second a parallel plane to an outer nare surface and a parallel plane to said nasal midline; an angle formed between a parallel plane to a first outer nostril and a plane parallel to a nasal midline versus a distance between a parallel plane to a second outer nostril and a parallel plane to said nasal midline; an angle formed between a parallel plane to a first inner nostril and a plane parallel to a nasal midline versus a distance between a parallel plane to a second inner nostril and a parallel plane to said nasal midline; a curvature measurement of a first nostril, a curvature measurement of a second nostril; a curvature measurement of a tip of a nose; or any combination thereof.

Referring to FIG. 5, for example, for a given capture image, the width of 10 and 20 may be derived serving as a user standard and similarly, the distance between an outer nare surface and inner nostril boundary may be determined from a captured image of a putative user and compared to the standard, alone or in combination with various additional measured values, such as comparing 35 and 25 of a user standard, versus a distance between an outer nostril boundary and inner nostril boundary of a captured image.

In some aspects, the width of 10+35+85+90, and 95+100+25+20 is calculated for a captured image and compared to the width/distance of the first outer nare surface and a nasal midline and second outer nare surface and a nasal midline for a user standard, etc.

In some aspects, the use of multiple cameras and multiple positioning of the same provides for depth perception and measurements, which in turn may also be used as part of the authentication match data compiled in accordance with the uses, devices and methods of this invention.

It will be appreciated that any number of permutations of the above is envisioned including curvature and angle measurements as described.

It will be appreciated that values matching from evaluations of a captured image versus a user standard for a single point would be considered to represent a one-point match, i.e. one identifier point has provided a matching value. In some aspects, user identification relies on at least a three-point, or in some embodiments, at least a four-point, or in some embodiments, at least a five-point, or in some embodiments, at least a six-point, or in some embodiments, at least a seven-point, or in some embodiments, at least an eight-point, or in some embodiments, at least a nine-point, or in some embodiments, at least a ten-point, or in some embodiments, at least a ten or more-point match.

In some embodiments, the dosage form dispensing mechanism comprises:
  a secured, enclosed compartment adapted for containing at least one dosage form;
  an positioner for positioning said secured, enclosed compartment adapted for containing at least one dosage form to be operationally positioned to a selective depilling mechanism;
  a selective depilling mechanism which releases said at least one dosage form from said secured, enclosed compartment; and
  a conveyor, operationally connected to said selective depilling mechanism whereby release of said at least one dosage form allows for retention of same on or in said conveyor In some embodiments, the interface connected to the dispensing mechanism connects to the positioner, promoting positioning of the at least one dosage form with respect to the selective depilling mechanism when authentication has been obtained.

In some embodiments, the interface connects to the selective depilling mechanism, which activates said depilling mechanism when said authentication has been obtained.

In some embodiments, the dispenser further comprises an outlet connected to said conveyor and configured for engagement and selective actuation by the mouth of a user, promoting egress of said at least one dosage form from said dosage form dispensing mechanism into the oral cavity of said subject.

In some embodiments, the dosage form dispenser further comprises a power source connected to said microprocessor and said memory and optionally said power source is further connected to a circuit connected to said dosage form dispensing mechanism, or positioner; a display; a pill counter; or a communication bus or any combination thereof.

This invention provides, in some embodiments, a method for dispensing a dosage form directly within an oral cavity of a subject in need thereof, said method comprising:
  Inserting a first portion of a casing of a dosage form dispenser adapted for insertion within an oral cavity of said subject, wherein said dosage form dispenser further comprises
    a second portion of said casing;
    at least one camera positioned on said second portion, further positioned to capture a field of view of a portion of a face of a subject, wherein said field of view comprises at least a portion of a base view of the nose of said subject;

a dosage form dispensing mechanism;

a microprocessor and associated memory for processing and storing user authentication information, comparing images relayed from said at least one camera to at least one stored user standard and providing authentication when a match is established; and an interface connected to said dispensing mechanism, which promotes dispensing said dosage form when said authentication has been obtained;

activating said at least one camera to capture a field of view of a portion of a face of said subject;

activating said microprocessor to compare at least one image related from said at least one camera to at least one stored user standard and providing authentication when a match therebetween is established; and activating said interface to promote dispensing said dosage form when said authentication has been obtained.

In some embodiments, the second portion of the casing is angled, with respect to said first portion.

In some embodiments, the dosage form dispensing mechanism comprises:

a secured, enclosed compartment adapted for containing at least one dosage form;

an positioner for positioning said secured, enclosed compartment adapted for containing at least one dosage form to be operationally positioned to a selective depilling mechanism;

a selective depilling mechanism which releases said at least one dosage form from said secured, enclosed compartment; and a conveyor, operationally connected to said selective depilling mechanism whereby release of said at least one dosage form allows for retention of same on or in said conveyor In some embodiments, the interface connects to said positioner, promoting positioning of said at least one dosage form with respect to said selective depilling mechanism when said authentication has been obtained.

In some embodiments, the interface connects to said selective depilling mechanism, which activates said depilling mechanism when said authentication has been obtained In some embodiments, the dispenser further comprises an outlet connected to said conveyor and configured for engagement and selective actuation by the mouth of a user, promoting egress of said at least one dosage form from said dosage form dispensing mechanism into the oral cavity of said subject.

In some embodiments, the at least one dosage form is contained within a blister package, which comprises a covered cavity bounded by a backing containing a dosage form therewithin.

In some embodiments, the selective depilling mechanism comprises a double action depilling mechanism, comprising a first pusher, sized and adapted to engage a top surface of said covered cavity and to exert a first sufficient force thereagainst so as to push said dosage form contained therein against its respective bounding backing, and a second pusher sized and adapted to more forcibly engage said top surface of said covered cavity and to exert a second sufficient force thereagainst so as to expel said dosage form from said blister.

In some embodiments, the blister package comprises an array of dosage forms.

In some embodiments, the array comprises at least one linear column of dosage forms or at least one circular distribution of dosage forms.

In some embodiments, the casing comprises two or three cameras positioned on said second portion and proximal to said first portion of said casing.

In some embodiments, the casing further comprises at least one light source positioned on said second portion.

In some embodiments, the light source facilitates improved image capture from said at least one camera, improved user experience with said dispenser or a combination thereof.

In some embodiments, the at least one camera has a zoom feature.

In some embodiments, the dispenser further comprises a real-time clock for generating time signals which signals are processed and compared to a pre-set time schedule and can override activation of positioning of said at least one dosage form or activation of said depilling mechanism if the time signals processed do not match said pre-set time schedule.

In some embodiments, the dispenser further comprises a user alert indicator operationally coupled to said real-time clock, which alerts said subject about a scheduled time for dispensing said dosage form.

In some embodiments, the processing said user authentication information may comprise rotating or skewing images relayed from said at least one camera prior to or while comparing same to said at least one stored user standard.

In some embodiments, the stored user standard may be a compilation of user images captured and stored over time.

In some embodiments, the stored user standard may comprise a weighted determination introducing a bias in favor of more recently stored images.

In some embodiments, the processing said user authentication information may comprise using aging algorithms.

In some embodiments, the processing said user authentication information may comprise establishing at least a two-identifier point match between features identified from said portion of a base view of the nose of said subject as compared to said stored user standard.

In some embodiments, the processing said user authentication information may comprise establishing a three-identifier point to ten-identifier point match between features identified from said portion of a base view of the nose of said subject as compared to said stored user standard.

In some embodiments, the identifier point is a measurement comprising a distance between an outer nare surface and outer nostril boundary, a distance between an outer nare surface and inner nostril boundary; a distance between an outer nostril boundary and inner nostril boundary; a distance between a first outer nare surface and a second outer nare surface; a distance between a first outer nare surface and a nasal midline versus a distance between a second outer nare surface and said nasal midline; a distance between a first outer nostril and a nasal midline versus a distance between a second outer nostril and said nasal midline; a distance between a first inner nostril and a nasal midline versus a distance between a second inner nostril and said nasal midline; an angle formed between a parallel plane to a first outer nare surface and a plane parallel to a nasal midline versus a distance between a second a parallel plane to an outer nare surface and a parallel plane to said nasal midline; an angle formed between a parallel plane to a first outer nostril and a plane parallel to a nasal midline versus a distance between a parallel plane to a second outer nostril and a parallel plane to said nasal midline; an angle formed between a parallel plane to a first inner nostril and a plane parallel to a nasal midline versus a distance between a parallel plane to a second inner nostril and a parallel plane to said nasal midline; a curvature measurement of a first nostril, a curvature measurement of a second nostril; a curvature measurement of a tip of a nose; or any combination thereof.

In some embodiments, the one or more dosage forms may be contained within said secured, enclosed compartment.

In some embodiments, the dosage form dispenser further comprises a power source connected to said microprocessor and said memory and optionally said power source is further connected to a circuit connected to said dosage form dispensing mechanism, or positioner; a display; a pill counter; or a communication bus or any combination thereof.

Figure 6:
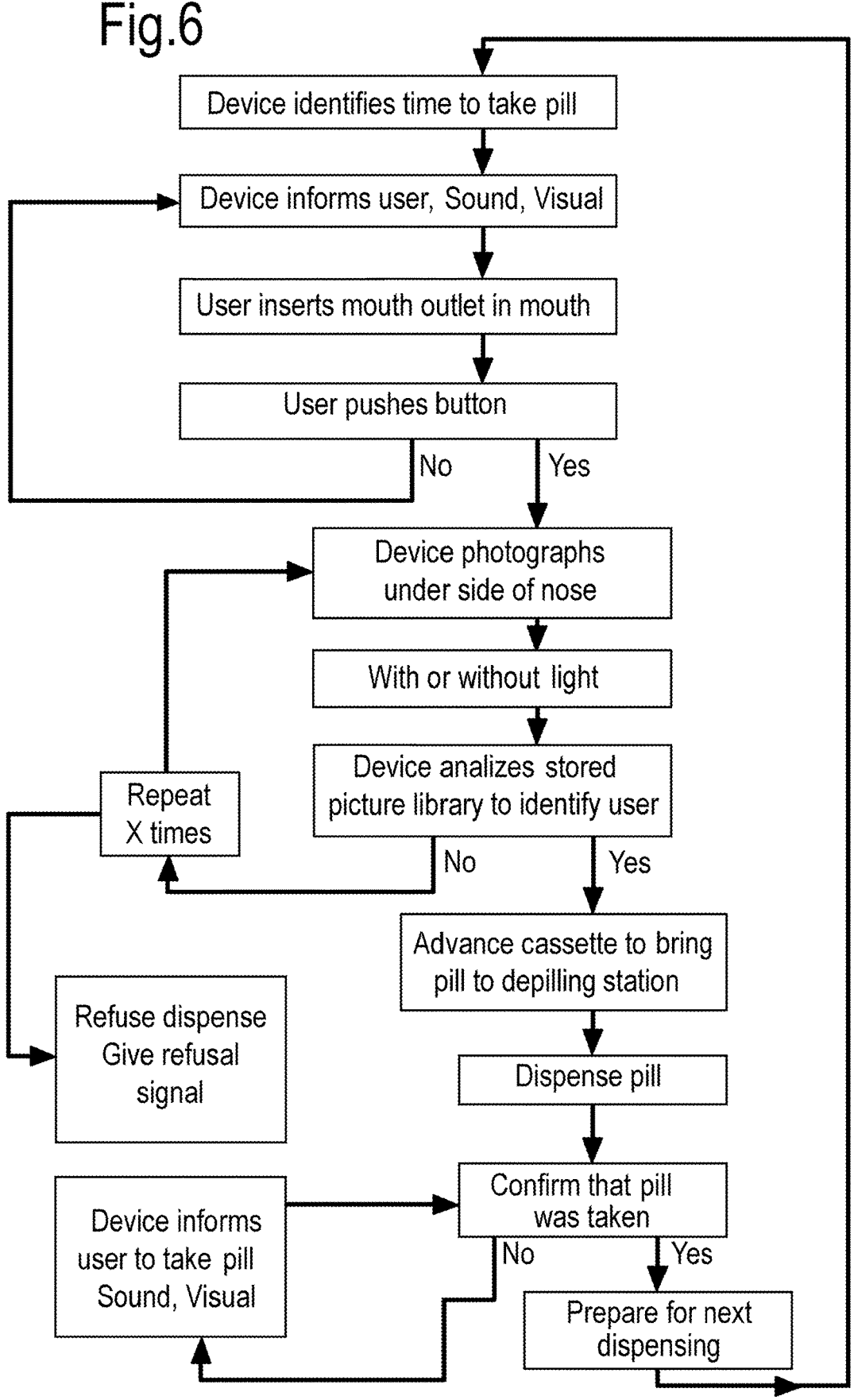
FIG. 6 schematically depicts an embodied protocol for using and authenticating the dispensing device of this invention.

Referring now to FIG. 6, an embodied flow chart is provided for use of the dosage form dispensers of this invention and/or encompassing aspects of the methods of this invention.

Figure 10:
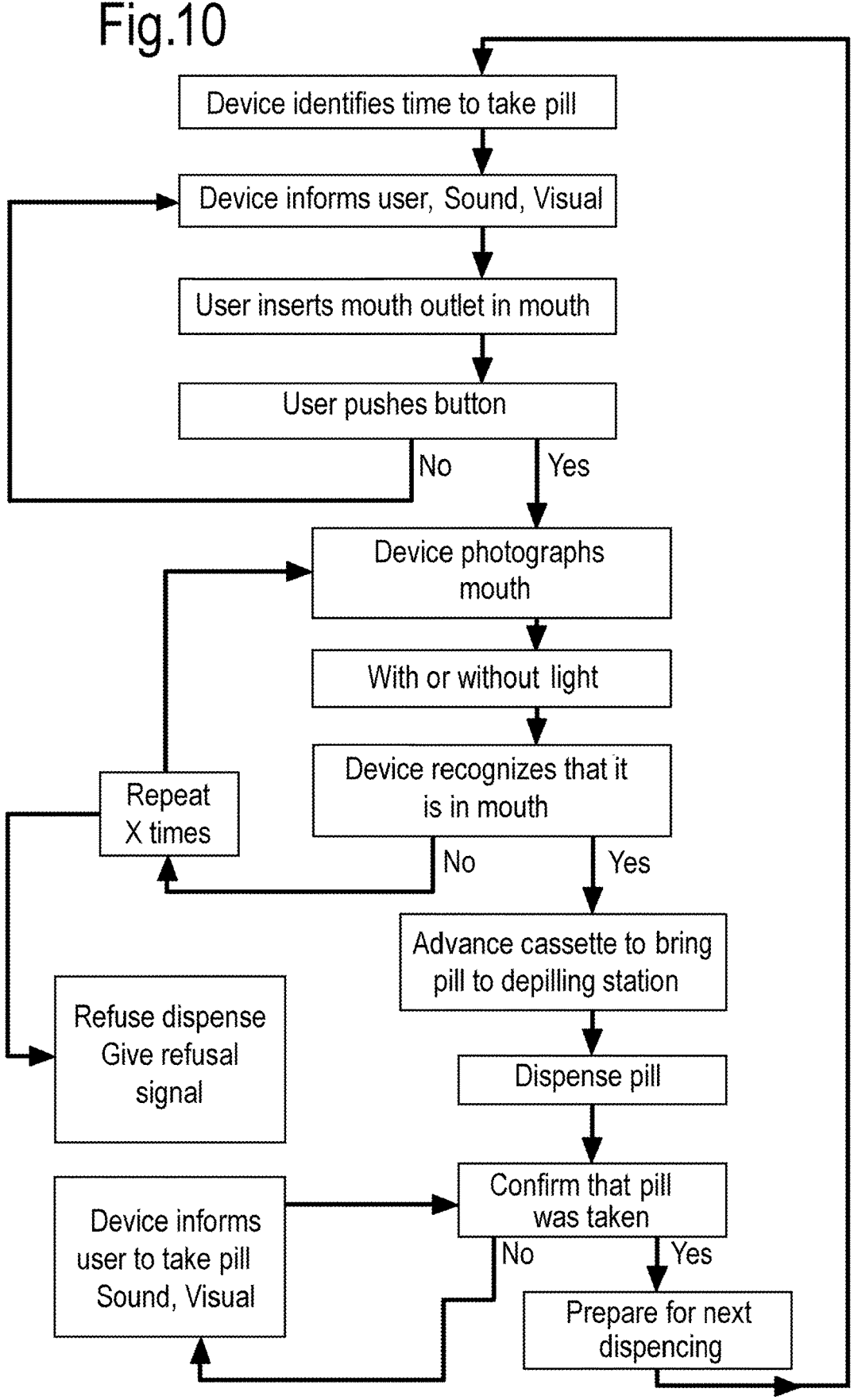
FIG. 10 schematically depicts an embodied protocol for using and authenticating the dispensing device of this invention.

Similarly, FIG. 10 provides another flow chart describing various steps and aspects of the use of the dosage form dispensers of this invention and/or encompassing aspects of the methods of this invention.

In some aspects, the dispenser specifically provides a means to initiate a device run, based on a timed event, and then in some embodiments, provides a visual or sound alert for the user to engage the device. Upon receipt of the alert, the user will, in this aspect, insert the outlet of the first portion of the dispenser within his or her mouth.

In some aspects, the user must positively continue with drug dispensing by activating the device, e.g. by pushing a button. In some aspects, failure to engage the button at the indicated time will result in repeat issuance of the visual or sounded alert.

In some aspects, it may further engage or relay a command for an off-site action, for example, via contact of a responsible health proxy or medical aid worker.

In some aspects, the failure to engage the button may also signal a compromised or breached protocol whereby an incorrect user has gained access to the dispenser and the same may trigger an alert, for example, relaying a command for an off-site action, for example, via contact of a responsible health proxy or medical aid worker.

The user may also properly activate the device, for example, by engaging or pushing an appropriate switch/button on the dispenser.

According to this aspect, and in some embodiments, such activation may in turn activate the camera to acquire an image/capture a field of view of a portion of a face of a subject, which field of view comprises at least a portion of a base view of the nose of the user.

In some aspects, the dispenser may capture such image with or without the aid of a light source or both.

In some aspects, the microprocessor promotes comparing such captured images relayed from the at least one camera to captured images of a stored user standard. In some aspects, the microprocessor promotes comparing such values obtained and considered to serve as identifier point matches of standard features, for establishing, e.g. an at least two-identifier point match between features identified from said portion of a base view of the nose of said subject as compared to said stored user standard.

In some aspects, the match is established via set criteria and serves as providing authentication for the match being established.

In some aspects, if the authentication protocol fails, there is an attempt to repeat the capture image process a defined number of times.

In some aspects, if the authentication protocol fails beyond a defined number of times, then the dispenser will not provide for dispensing of the oral dosage form contained therein, and in some embodiments, the dispenser may provide a means to further engage or relay a command for an off-site action, for example, via contact of a responsible health proxy or medical aid worker.

In some embodiments, authentication being achieved promotes advancing of an oral dosage form to an appropriate dispensing station, for example, by advancing a cassette to position an oral dosage form operable releasable by a now engaged depilling station.

In some embodiments, once the dosage form is appropriately engaged it is dispensed into the mouth of the user, via the first portion already positioned within the mouth of the user, as noted hereinabove.

In some aspects, the dispenser may further comprise a sensor which in turn can sense whether the dosage form released from its containment apparatus has been extracted from the dispenser into the mouth of the user.

According to this aspect and in some embodiments, failure to detect that the dosage form was placed appropriately within the mouth of the user engages an alarm, e.g. a visual or sounded alarm to alert the user to properly ingest the dosage form.

In some aspects, the sensor detects correct ingestion or taking of the dosage form into the mouth of the user, and same sets the device to be at the ready for the next indicated time of drug dispensing.

In some aspects the dispenser may further comprise any type of data entry and/or communication modules, such as, but not limited, to visual display screen, a standard or miniaturized alphanumeric key board, a mouse or pointing device, a touch screen, a speaker, a microphone, a voice recognition device, a communication port such as a wireless communication port, and any combinations thereof.

In this manner, in some aspects, the user may further, for example, input personal information, which may also enhance the security function of the dispensers of this invention.

In some aspects, the dosage form dispenser has one or more specific locking mechanisms configured to prevent advancing a dosage form in said dispenser to a position for dispensing of same, in the absence of a specific authentication protocol match as defined. Such locking mechanisms, in turn, may include any configuration of parts to accomplish same, such as, for example, bias pins or catches, between movable advancing parts of the dispenser. In some aspects, a relay mechanism provides for such locking mechanism to be communicatively interconnected to the processor and can be configured to position same in the closed position or the open position upon receipt of an appropriate command/code from the processor, following authentication.

In some embodiments, the sensor(s) may be communicatively interconnected with a counter and/or the processor. The sensor(s) may be any type of sensor, such as a movement or motion sensor, a proximity sensor, a plunger sensor, a limit switch, etc. Additional sensors may be included in the dispenser to detect other occurrences, such as a sensor to detect whether the power source has available power that falls below a predetermined threshold, a sensor to detect whether the dosage form containing element is secured appropriately to the casing, etc.

In some embodiments, the dosage form dispenser has one or more display(s), and in some embodiments, a key or button to illuminate the display, and in some embodiments, a visual indicator, and in some embodiments, an audible indicator, and in some embodiments, input/output interfaces.

In some aspects, the display can, inter alia, indicate a low power source signal, a counter for dosage forms dispensed, a counter for dosage forms remaining, a time of last confirmed dosage, etc. The visual indicator can, in some embodiments, flash in a desired color, e.g., red, green, etc., to indicate when it is time for a pill to be taken. The audible indicators can emit an audible sound when it is time for the pill to be taken. The input/output interfaces may, in some embodiments, comprise four keys, buttons, or toggle switches that may be color-coded and/or may include indicia to enable a user to, for example, also enter a PIN as an additional safety measure in the authentication protocol.

In some aspects, the dispensers of this invention will have visual and/or audio indicators. In some aspects, the visual indicator(s) are configured to provide a visual indication to remind the user to dispense a pill from the dispenser, to indicate the time, to indicate the status of the power source, or the like. The visual indicator(s), in some aspects, may emit light to provide the visual indication and in some embodiments, are light emitting diodes (LEDs) of any desired color, but may be any type of light.

In some aspects, the audible indicator(s) are configured to emit a distinctive audible sound, and may be a speaker that is powered by an amplifier to emit a buzzer, chirp, chime, or the like. Alternatively, the audible indicator may be a speaker that relays audible communication information, such as a recorded message, a relayed communication message, a relayed live transmission, or the like.

In some aspects, the dispensers of this invention will have physical indicators, as well. In some aspects, the physical indicator(s) is configured to produce a physical movement of the dispenser, such as a vibration or the like.

In some aspects, the dispenser power source may be any appropriate source, for example, a thin lithium battery, or comprising one or more batteries (rechargeable or non-rechargeable) or the like, and may be removable or non-removable.

In some aspects, the dispenser memory and processor are configured in the form of a microcontroller, control logic, firmware, or other dispensing circuitry.

In some aspects, the memory stores instructions and data, such as the user profile information including weighted user profile information as described hereinabove, as processed information and includes some form of dispensing software embodied thereon. The memory may be configured on any type of volatile or non-volatile medium, such as Flash memory, EEPROM memory, dynamic RAM memory, parameter RAM memory, or the like.

In some aspects, the processor may connect to all of the components on the dispenser and controls the movement and process of instructions as well as data in the dispenser. In some aspects, the memory and processor may be programmed internally by the input/output interface(s) and/or externally wirelessly or non-wirelessly using a remote computer device via a transceiver(s) and antenna or through input/output port(s) or any appropriate means, as will be appreciated by the skilled artisan.

In some aspects, the dispenser is configured to logically interconnect wirelessly to a remote computer device via, for example, a transceiver and antenna, or non-wirelessly to a remote computer device via input/output port(s). Wireless interconnection may occur via any known technique (e.g., wireless local area network (LAN), IrDA, Bluetooth, FireWire, etc.). Non-wireless interconnection may occur through a network system via any number of switches, such as a LAN, a wide area network (WAN), an intranet, an extranet, the Internet, etc. Any type of a remote computer device may be interconnected with the dispenser, such as a desk top computer, a laptop computer, personal digital assistant (PDA), a cell phone, a remote control, a pager, etc.

In some aspects, the dosage form dispenser may further comprise a real time clock serving as a timing mechanism to provide timing data corresponding to particular occurrences associated with the sensor(s). For example, when the dispensing mechanism dispenses an oral dosage form following authentication, the associated sensor(s) may in some embodiments, provide a signal of the dispensing activity, whereupon the processor obtains timing data from the real time clock and stores the timing data in the memory.

According to this aspect, and in some embodiments, the display may be configured as a liquid crystal display (LCD), but may be any type of electronic display as desired. The display(s) may be configured to be illuminated and one of the input/output interfaces, e.g., a button key, toggle switch, etc., may be configured to turn the display(s) on and off.

It will be appreciated that this invention provides a versatile dosage form delivery device facilitating deposition of a dosage form within an oral cavity of a subject, following authentication by an established protocol via a unit promoting mobility for the subject, in a home care setting.

It should also be noted that the terms "first", "second", "third", "upper", "lower", and the like may be used herein to modify various elements. These modifiers do not imply a spatial, sequential, or hierarchical order to the modified elements unless specifically stated.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of the appended claims.

What is claimed is:

1. A dosage form dispenser, comprising:
   a casing comprising a first portion adapted for insertion within an oral cavity of a subject and a second portion adapted to encase a dosage form dispensing mechanism located therewithin;
   at least one camera contained on or within the dosage form dispenser and positioned on said second portion of said casing, and further positioned to capture a field of view of a portion of a face of a subject, wherein said field of view comprises at least a portion of a base view of the nose of said subject, the at least one camera configured to capture the field of view while the first portion is located underneath the nose of the subject;
   a dosage form dispensing mechanism;
   a microprocessor and associated memory for processing and storing user authentication information, comparing images relayed from said at least one camera to at least one stored user standard and providing authentication when a match is established; and an interface connected to said dispensing mechanism, which promotes dispensing said dosage form when said authentication has been obtained.

2. The dosage form dispenser of claim 1, wherein said second portion of said casing is angled with respect to said first portion.

3. The dosage form dispenser of claim 1, wherein said at least one camera is positioned on said second portion, proximal to said first portion of said casing.

4. The dosage form dispenser of claim 1, wherein said casing comprises two or three cameras positioned on said second portion and proximal to said first portion of said casing.

5. The dosage form dispenser of claim 1, wherein said casing further comprises at least one light source positioned on said second portion.

6. The dosage form dispenser of claim 5, wherein said light source facilitates improved image capture from said at least one camera, improved user experience with said dispenser or a combination thereof.

7. The dosage form dispenser of claim 1, wherein said at least one camera has a zoom feature.

8. The dosage form dispenser of claim 1, wherein processing said user authentication information may comprise rotating or skewing images relayed from said at least one camera prior to, or while comparing same to, said at least one stored user standard.

9. The dosage form dispenser of claim 1, wherein said stored user standard may be a compilation of user images captured and stored over time, wherein said stored user standard may comprise a weighted determination introducing a bias in favor of more recently stored images.

10. The dosage form dispenser of claim 1, wherein processing said user authentication information may comprise using aging algorithms.

11. The dosage form dispenser of claim 1, wherein processing said user authentication information may comprise establishing at least a two-identifier point match between features identified from said portion of a base view of the nose of said subject as compared to said stored user standard, wherein processing said user authentication information may comprise establishing a three-identifier point to ten-identifier point match between features identified from said portion of a base view of the nose of said subject as compared to said stored user standard; or
wherein said identifier point is a measurement comprising a distance between an outer nare surface and outer nostril boundary, a distance between an outer nare surface and inner nostril boundary; a distance between an outer nostril boundary and inner nostril boundary; a distance between a first outer nare surface and a second outer nare surface; a distance between a first outer nare surface and a nasal midline versus a distance between a second outer nare surface and said nasal midline; a distance between a first outer nostril and a nasal midline versus a distance between a second outer nostril and said nasal midline; a distance between a first inner nostril and a nasal midline versus a distance between a second inner nostril and said nasal midline; an angle formed between a parallel plane to a first outer nare surface and a plane parallel to a nasal midline versus a distance between a second a parallel plane to an outer nare surface and a plane parallel to said nasal midline; an angle formed between a parallel plane to a first outer nostril and a plane parallel to a nasal midline versus a distance between parallel plane to a second outer nostril and a parallel plane to said nasal midline; an angle formed between a parallel plane to a first inner nostril and a plane parallel to a nasal midline versus a distance between a parallel plane to a second inner nostril and a parallel plane to said nasal midline; a curvature measurement of a first nostril, a curvature measurement of a second nostril; a curvature measurement of a tip of a nose; or any combination thereof.

12. The dosage form dispenser of claim 1, further comprising a power source connected to said microprocessor and said memory and optionally said power source is further connected to a circuit connected to said dosage form dispensing mechanism; a display; a pill counter; or a communication bus or any combination thereof.

13. The dosage form dispenser of claim 1, further comprising at least one camera positioned on a first portion of said casing, which camera is positioned to capture a field of view of a portion of an oral cavity of a subject, wherein said field of view comprises at least a portion of a top view or a base view of an oral cavity of a subject, or a combination thereof.

14. A method for dispensing a dosage form directly within an oral cavity of a subject in need thereof, said method comprising:
inserting a first portion of a casing of a dosage form dispenser adapted for insertion within an oral cavity of said subject,
wherein said dosage form dispenser further comprises
a second portion of said casing;
at least one camera contained on or within the dosage form dispenser and positioned on said second portion, and further positioned to capture a field of view of a portion of a face of a subject, wherein said field of view comprises at least a portion of a base view of the nose of said subject;
a dosage form dispensing mechanism;
a microprocessor and associated memory for processing and storing user authentication information, comparing images relayed from said at least one camera to at least one stored user standard and providing authentication when a match is established; and
an interface connected to said dispensing mechanism, which promotes dispensing said dosage form when said authentication has been obtained;
activating said at least one camera to capture a field of view of a portion of a face of said subject while the first portion is located underneath the nose of the subject;
activating said microprocessor to compare at least one image related from said at least one camera to at least one stored user standard and providing authentication when a match therebetween is established; and
activating said interface to promote dispensing said dosage form when said authentication has been obtained; and optionally wherein said identifier point is a measurement comprising a distance between an outer nare surface and outer nostril boundary, a distance between an outer nare surface and inner nostril boundary; a distance between an outer nostril boundary and inner nostril boundary; a distance between a first outer nare surface and a second outer nare surface; a distance between a first outer nare surface and a nasal midline versus a distance between a second outer nare surface and said nasal midline; a distance between a first outer nostril and a nasal midline versus a distance between a second outer nostril and said nasal midline; a distance between a first inner nostril and a nasal midline versus a distance between a second inner nostril and said nasal midline; an angle formed between a parallel plane to a first outer nare surface and a plane parallel to a nasal midline versus a distance between a second a parallel plane to an outer nare surface and a parallel plane to said nasal midline; an angle formed between a parallel plane to a first outer nostril and a plane parallel to a nasal midline versus a distance between a parallel plane to a second outer nostril and a parallel plane to said nasal midline; an angle formed between a parallel plane to a first inner nostril and a plane parallel to a nasal midline versus a distance between a parallel plane to a second inner nostril and a parallel plane to said nasal midline; a curvature measurement of a first nostril, a curvature measurement of a second nostril; a curvature measurement of a tip of a nose; or any combination thereof.

15. The method of claim 14, wherein processing said user authentication information may comprise rotating or skewing images relayed from said at least one camera prior to or while comparing same to said at least one stored user standard.

16. The method of claim 14, wherein said stored user standard may be a compilation of user images captured and stored over time.

17. The method of claim 14, wherein said stored user standard may comprise a weighted determination introducing a bias in favor of more recently stored images.

18. The method of claim 14, wherein processing said user authentication information may comprise using aging algorithms.

19. The method of claim 14, wherein processing said user authentication information may comprise establishing at least a two-identifier point match between features identified from said portion of a base view of the nose of said subject as compared to said stored user standard; and optionally wherein said identifier point is a measurement comprising a distance between an outer nare surface and outer nostril boundary, a distance between an outer nare surface and inner nostril boundary; a distance between an outer nostril boundary and inner nostril boundary; a distance between a first outer nare surface and a second outer nare surface; a distance between a first outer nare surface and a nasal midline versus a distance between a second outer nare surface and said nasal midline; a distance between a first outer nostril and a nasal midline versus a distance between a second outer nostril and said nasal midline; a distance between a first inner nostril and a nasal midline versus a distance between a second inner nostril and said nasal midline; an angle formed between a parallel plane to a first outer nare surface and a plane parallel to a nasal midline versus a distance between a second a parallel plane to an outer nare surface and a parallel plane to said nasal midline; an angle formed between a parallel plane to a first outer nostril and a plane parallel to a nasal midline versus a distance between a parallel plane to a second outer nostril and a parallel plane to said nasal midline; an angle formed between a parallel plane to a first inner nostril and a plane parallel to a nasal midline versus a distance between a parallel plane to a second inner nostril and a parallel plane to said nasal midline; a curvature measurement of a first nostril, a curvature measurement of a second nostril; a curvature measurement of a tip of a nose; or any combination thereof.

20. The method of claim 14, wherein processing said user authentication information may comprise establishing a three-identifier point to ten-identifier point match between features identified from said portion of a base view of the nose of said subject as compared to said stored user standard; and optionally wherein said identifier point is a measurement comprising a distance between an outer nare surface and outer nostril boundary, a distance between an outer nare surface and inner nostril boundary; a distance between an outer nostril boundary and inner nostril boundary; a distance between a first outer nare surface and a second outer nare surface; a distance between a first outer nare surface and a nasal midline versus a distance between a second outer nare surface and said nasal midline; a distance between a first outer nostril and a nasal midline versus a distance between a second outer nostril and said nasal midline; a distance between a first inner nostril and a nasal midline versus a distance between a second inner nostril and said nasal midline; an angle formed between a parallel plane to a first outer nare surface and a plane parallel to a nasal midline versus a distance between a second a parallel plane to an outer nare surface and a parallel plane to said nasal midline; an angle formed between a parallel plane to a first outer nostril and a plane parallel to a nasal midline versus a distance between a parallel plane to a second outer nostril and a parallel plane to said nasal midline; an angle formed between a parallel plane to a first inner nostril and a plane parallel to a nasal midline versus a distance between a parallel plane to a second inner nostril and a parallel plane to said nasal midline; a curvature measurement of a first nostril, a curvature measurement of a second nostril; a curvature measurement of a tip of a nose; or any combination thereof.

21. A dosage form dispenser, comprising:
a casing comprising a first portion adapted for insertion within an oral cavity of a subject and a second portion adapted to encase a dosage form dispensing mechanism located therewithin;
at least one camera contained on or within the dosage form dispenser and positioned on said first portion of said casing, and further positioned to capture a field of view of a portion of an oral cavity of a subject, wherein said field of view comprises at least a portion of a top view or a base view of an oral cavity of a subject, or a combination thereof, the at least one camera configured to capture the field of view while the first portion is located underneath the nose of the subject;
a dosage form dispensing mechanism;
a microprocessor and associated memory for processing and storing user authentication information, comparing images relayed from said at least one camera to at least one stored user standard and providing authentication when a match is established; and
an interface connected to said dispensing mechanism, which promotes dispensing said dosage form when said authentication has been obtained.

22. The dosage form dispenser of claim 21, comprising:
a casing comprising a first portion adapted for insertion within an oral cavity of a subject and a second portion adapted to encase a dosage form dispensing mechanism located therewithin;
at least one camera positioned on said first portion of said casing, further positioned to capture a field of view of a portion of an oral cavity of a subject, wherein said field of view comprises at least a portion of a top view or a base view of an oral cavity of a subject, or a combination thereof;
a dosage form dispensing mechanism;
a microprocessor and associated memory for processing and storing user authentication information, comparing images relayed from said at least one camera to at least one stored user standard and providing authentication when a match is established; and an interface connected to said dispensing mechanism, which promotes dispensing said dosage form when said authentication has been obtained.

23. The dosage form dispenser of claim 21, wherein said casing comprises two or three cameras positioned on said first portion on a top surface of said casing, or on a bottom surface of said casing, or a combination thereof.

24. The dosage form dispenser of claim 21, wherein said casing further comprises at least one light source positioned on said first portion, wherein said light source facilitates improved image capture from said at least one camera, improved user experience with said dispenser or a combination thereof.

25. The dosage form dispenser of claim 21, wherein processing said user authentication information may comprise rotating or skewing images relayed from said at least one camera prior to or while comparing same to said at least one stored user standard.

26. The dosage form dispenser of claim 21, wherein said stored user standard may be a compilation of user images captured and stored over time, or
  wherein said stored user standard may comprise a weighted determination introducing a bias in favor of more recently stored images, or
  wherein one or more dosage forms may be contained within said enclosed compartment.

27. The dosage form dispenser of claim 21, further comprising a power source connected to said microprocessor and said memory and optionally said power source is further connected to a circuit connected to said dosage form dispensing mechanism; a display; a pill counter; or a communication bus or any combination thereof.

28. A method for dispensing a dosage form directly within an oral cavity of a subject in need thereof, said method comprising:
  Inserting a first portion of a casing of a dosage form dispenser adapted for insertion within an oral cavity of said subject, wherein said dosage form dispenser further comprises
    a second portion of said casing;
    at least one camera contained on or within the dosage form dispenser and positioned on said first portion, and further positioned to capture a field of view of a portion of an oral cavity of a subject, wherein said field of view comprises at least a portion of a top view or a base view of an oral cavity of a subject, or a combination thereof;
    a dosage form dispensing mechanism;
    a microprocessor and associated memory for processing and storing user authentication information, comparing images relayed from said at least one camera to at least one stored user standard and providing authentication when a match is established; and
    an interface connected to said dispensing mechanism, which promotes dispensing said dosage form when said authentication has been obtained;
  activating said at least one camera to capture a field of view of a portion of a face of said subject while the first portion is located underneath the nose of the subject;
  activating said microprocessor to compare at least one image related from said at least one camera to at least one stored user standard and providing authentication when a match therebetween is established; and
  activating said interface to promote dispensing said dosage form when said authentication has been obtained.

29. The method of claim 28, wherein processing said user authentication information may comprise rotating or skewing images relayed from said at least one camera prior to or while comparing same to said at least one stored user standard.

30. The method of claim 28, wherein said stored user standard may be a compilation of user images captured and stored over time.

31. The method of claim 28, wherein said stored user standard may comprise a weighted determination introducing a bias in favor of more recently stored images.

* * * * *

UNITED STATES PATENT AND TRADEMARK OFFICE
CERTIFICATE OF CORRECTION

| | | |
|---|---|---|
| PATENT NO. | : 11,264,125 B2 | Page 1 of 1 |
| APPLICATION NO. | : 15/768459 | |
| DATED | : March 1, 2022 | |
| INVENTOR(S) | : Paz | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 705 days.

Signed and Sealed this
Eleventh Day of February, 2025

Coke Morgan Stewart
*Acting Director of the United States Patent and Trademark Office*